United States Patent
Boswell et al.

(10) Patent No.: US 10,751,266 B2
(45) Date of Patent: Aug. 25, 2020

(54) METHOD OF MAKING A BARRIER PATCH WITH SOLUBLE FILM

(71) Applicant: The Procter & Gamble Company, Cincinnati, OH (US)

(72) Inventors: Emily Charlotte Boswell, Cincinnati, OH (US); Elizabeth Anne Wilder, West Chester, OH (US); Jack Alan Hunter, Springboro, OH (US); Edward Daniel Theiss, III, Union Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 56 days.

(21) Appl. No.: 16/358,225

(22) Filed: Mar. 19, 2019

(65) Prior Publication Data
US 2019/0282459 A1    Sep. 19, 2019

Related U.S. Application Data

(60) Provisional application No. 62/644,707, filed on Mar. 19, 2018.

(51) Int. Cl.
*A61K 8/00* (2006.01)
*A61K 9/00* (2006.01)
(Continued)

(52) U.S. Cl.
CPC .............. *A61K 8/0208* (2013.01); *A61K 8/06* (2013.01); *A61K 8/19* (2013.01); *A61K 8/34* (2013.01);
(Continued)

(58) Field of Classification Search
CPC ... A61K 8/00; A61K 8/02; A61K 8/02; A61K 8/0208; A61K 8/06; A61K 8/10;
(Continued)

(56) References Cited

U.S. PATENT DOCUMENTS 3,155,034 A    11/1964 Reinke
3,482,300 A    12/1969 Reinke
(Continued)

FOREIGN PATENT DOCUMENTS

EP    0238200 A2    9/1987
EP    0904049 B1    6/2001
(Continued)

OTHER PUBLICATIONS

All Office Actions, U.S. Appl. No. 14/919,048.
(Continued)

*Primary Examiner* — Jacob T Minskey
*Assistant Examiner* — Matthew Hoover
(74) *Attorney, Agent, or Firm* — John G. Powell

(57) ABSTRACT

A method of producing a multi-layer beauty care product for applying a skin active agent to the skin. The method involves applying a water-soluble fluid to a transfer substrate. The water-soluble fluid contains a skin active agent and is applied to the transfer substrate through an image carrier having a mesh size of 40 to 500. The water-soluble fluid is dried to form a water-soluble film, which is then transferred to a backing layer coated with a pressure sensitive adhesive. The resulting multi-layer beauty care product provides a suitable a means of delivering the skin care active agent to a target portion of skin.

19 Claims, 7 Drawing Sheets

(51) Int. Cl.

| | | |
|---|---|---|
| *A61Q 19/00* | (2006.01) | |
| *A61K 8/02* | (2006.01) | |
| *A61K 8/86* | (2006.01) | |
| *A61K 8/73* | (2006.01) | |
| *A61K 8/34* | (2006.01) | |
| *A61K 8/42* | (2006.01) | |
| *A61K 8/19* | (2006.01) | |
| *A61K 8/49* | (2006.01) | |
| *A61K 8/06* | (2006.01) | |
| *A61Q 19/08* | (2006.01) | |
| *A61K 9/70* | (2006.01) | |
| *A61Q 19/02* | (2006.01) | |

(52) U.S. Cl.
CPC .............. *A61K 8/42* (2013.01); *A61K 8/4926* (2013.01); *A61K 8/731* (2013.01); *A61K 8/86* (2013.01); *A61K 9/703* (2013.01); *A61K 9/7023* (2013.01); *A61K 9/7084* (2013.01); *A61Q 19/00* (2013.01); *A61Q 19/02* (2013.01); *A61Q 19/08* (2013.01); *A61K 2800/805* (2013.01)

(58) Field of Classification Search
CPC ... A61K 8/19; A61K 8/30; A61K 8/34; A61K 8/40; A61K 8/42; A61K 8/49; A61K 8/492; A61K 8/4926; A61K 8/70; A61K 8/73; A61K 8/731; A61K 8/80; A61K 8/86; A61K 9/00; A61K 9/70; A61K 9/702; A61K 9/7023; A61K 9/703; A61K 9/708; A61K 9/7084; A61Q 19/00; A61Q 19/02; A61Q 19/08
See application file for complete search history.

(56) References Cited

U.S. PATENT DOCUMENTS

| | | |
|---|---|---|
| 3,696,741 A | 10/1972 | Reinke |
| 3,759,799 A | 9/1973 | Reinke |
| 3,759,800 A | 9/1973 | Reinke |
| 4,341,209 A | 7/1982 | Schaar |
| 4,377,616 A | 3/1983 | Ashcraft et al. |
| 4,472,328 A | 9/1984 | Sugimoto et al. |
| 4,519,538 A | 5/1985 | Omichi |
| 4,578,297 A | 3/1986 | Duncan |
| 4,649,186 A | 3/1987 | Jenkins et al. |
| 4,699,792 A | 10/1987 | Nick et al. |
| 4,711,781 A | 12/1987 | Nick et al. |
| 4,725,439 A | 2/1988 | Campbell et al. |
| 4,743,249 A | 5/1988 | Loveland |
| 4,773,408 A | 9/1988 | Cilento et al. |
| 4,781,294 A | 11/1988 | Croce |
| 5,051,259 A | 9/1991 | Olsen et al. |
| 5,123,900 A | 6/1992 | Wick |
| 5,132,115 A | 7/1992 | Wolter et al. |
| 5,180,626 A | 1/1993 | Ishibashi et al. |
| 5,262,165 A | 11/1993 | Govil et al. |
| 5,387,450 A | 2/1995 | Stewart |
| 5,455,043 A | 10/1995 | Fischel-Ghodsian |
| 5,476,664 A | 12/1995 | Robinson et al. |
| 5,503,844 A | 4/1996 | Kwiatek et al. |
| 5,559,165 A | 9/1996 | Paul |
| 5,628,737 A | 5/1997 | Dobrin et al. |
| 5,629,014 A | 5/1997 | Kwiatek et al. |
| 5,641,506 A | 6/1997 | Talke et al. |
| 5,713,842 A | 2/1998 | Kay |
| 5,723,138 A | 3/1998 | Bae et al. |
| 5,785,978 A | 7/1998 | Porter et al. |
| 5,820,877 A | 10/1998 | Yamaguchi et al. |
| 5,958,447 A * | 9/1999 | Haralambopoulos ........................ A61K 9/7084 424/401 |
| 5,965,154 A | 10/1999 | Haralambopoulos |
| 5,968,533 A | 10/1999 | Porter et al. |
| 6,162,458 A | 12/2000 | Asada et al. |
| 6,168,028 B1 | 1/2001 | Telesca et al. |
| 6,183,770 B1 | 2/2001 | Muchin et al. |
| 6,200,596 B1 | 3/2001 | Schwartzmiller et al. |
| D440,315 S | 4/2001 | Hassenbein et al. |
| 6,221,369 B1 | 4/2001 | Pool et al. |
| 6,277,401 B1 | 8/2001 | Bello et al. |
| 6,325,565 B1 | 12/2001 | Girardot et al. |
| 6,338,855 B1 | 1/2002 | Albacarys et al. |
| 6,448,303 B1 | 9/2002 | Paul |
| 6,495,158 B1 | 12/2002 | Buseman et al. |
| 6,495,229 B1 | 12/2002 | Carte et al. |
| 6,593,602 B2 | 7/2003 | Liang et al. |
| D484,985 S | 1/2004 | Takizawa et al. |
| 6,673,363 B2 | 1/2004 | Luo et al. |
| 6,676,962 B1 | 1/2004 | Muller |
| 6,730,317 B2 | 5/2004 | Gueret |
| 6,899,840 B2 | 5/2005 | Ueda et al. |
| 6,926,960 B1 | 8/2005 | Hoshino et al. |
| 6,953,602 B2 | 10/2005 | Carte et al. |
| D519,239 S | 4/2006 | Katagiri |
| 7,063,859 B1 | 6/2006 | Kanios et al. |
| 7,256,234 B2 | 8/2007 | Nierle et al. |
| 7,531,185 B2 | 5/2009 | Chen et al. |
| 7,658,942 B2 * | 2/2010 | Deckner .............. A61K 8/0208 424/400 |
| 7,854,938 B2 | 12/2010 | Ueda et al. |
| 8,066,117 B2 | 11/2011 | Ueda et al. |
| 8,173,233 B2 | 5/2012 | Rogers et al. |
| 8,353,399 B2 | 1/2013 | Ueda et al. |
| 8,512,837 B2 | 8/2013 | Barreneche |
| 8,728,514 B2 | 5/2014 | Choi et al. |
| 9,066,888 B2 | 6/2015 | Kugelmann et al. |
| 2002/0022052 A1 | 2/2002 | Dransfield |
| 2002/0077266 A1 | 6/2002 | Gabriel et al. |
| 2002/0187181 A1 | 12/2002 | Godbey et al. |
| 2003/0072724 A1 | 4/2003 | Maibach et al. |
| 2003/0082219 A1 | 5/2003 | Warren et al. |
| 2003/0152610 A1 * | 8/2003 | Rolf .............. A61K 8/0212 424/449 |
| 2003/0167556 A1 | 9/2003 | Kelley |
| 2003/0175328 A1 | 9/2003 | Shefer et al. |
| 2003/0180347 A1 | 9/2003 | Young |
| 2004/0009202 A1 | 1/2004 | Woller |
| 2004/0116018 A1 | 6/2004 | Fenwick et al. |
| 2004/0202706 A1 | 10/2004 | Koo et al. |
| 2005/0013784 A1 | 1/2005 | Trigg et al. |
| 2005/0266059 A1 | 12/2005 | Poss |
| 2006/0104931 A1 | 5/2006 | Fukutome et al. |
| 2006/0121097 A1 | 6/2006 | Lodge et al. |
| 2006/0177487 A1 | 8/2006 | Martz |
| 2006/0198879 A1 | 9/2006 | Fukuta et al. |
| 2007/0020220 A1 | 1/2007 | Osborne |
| 2007/0060855 A1 | 3/2007 | Leung et al. |
| 2007/0254021 A1 | 11/2007 | Scimeca et al. |
| 2007/0259029 A1 | 11/2007 | McEntire et al. |
| 2007/0292491 A1 | 12/2007 | Hansen et al. |
| 2007/0298089 A1 | 12/2007 | Saeki et al. |
| 2008/0014231 A1 | 1/2008 | Okano |
| 2008/0138593 A1 | 6/2008 | Martinez |
| 2008/0260808 A1 | 10/2008 | Pinna et al. |
| 2009/0010998 A1 | 1/2009 | Marchitto et al. |
| 2009/0155326 A1 | 6/2009 | Mack et al. |
| 2009/0234308 A1 | 9/2009 | Jackson et al. |
| 2009/0249558 A1 | 10/2009 | Fileccia et al. |
| 2009/0258062 A1 | 10/2009 | Horstmann |
| 2009/0263600 A1 | 10/2009 | Miyashita et al. |
| 2009/0317578 A1 | 12/2009 | Rogers et al. |
| 2009/0317605 A1 | 12/2009 | Rogers et al. |
| 2010/0239619 A1 | 9/2010 | Hurwitz |
| 2011/0200652 A1 | 8/2011 | Smith et al. |
| 2011/0300198 A1 | 12/2011 | Nussinovitch et al. |
| 2012/0308619 A1 | 12/2012 | Tousley |
| 2013/0042417 A1 | 2/2013 | Smith et al. |
| 2013/0178407 A1 | 7/2013 | Fileccia et al. |
| 2014/0079938 A1 | 3/2014 | Perick et al. |
| 2014/0083878 A1 | 3/2014 | Tang et al. |
| 2014/0276478 A1 | 9/2014 | Liao et al. |

(56) References Cited

U.S. PATENT DOCUMENTS

| | | | |
|---|---|---|---|
| 2014/0376835 | A1 | 12/2014 | Rogers et al. |
| 2014/0377512 | A1 | 12/2014 | Rogers et al. |
| 2015/0209243 | A1 | 7/2015 | Shiroya et al. |
| 2015/0307264 | A1 | 10/2015 | Boswell et al. |
| 2015/0320606 | A1 | 11/2015 | Kawahara |
| 2016/0107004 | A1 | 4/2016 | Wilder et al. |
| 2017/0042311 | A1 | 2/2017 | Wilder et al. |
| 2017/0112724 | A1 | 4/2017 | Boswell et al. |
| 2017/0112725 | A1 | 4/2017 | Boswell et al. |
| 2017/0112726 | A1 | 4/2017 | Boswell et al. |
| 2017/0112727 | A1 | 4/2017 | Boswell et al. |
| 2018/0098921 | A1 | 4/2018 | Boswell et al. |
| 2018/0193229 | A1 | 7/2018 | Boswell et al. |
| 2018/0193230 | A1 | 7/2018 | Boswell et al. |
| 2018/0200158 | A1 | 7/2018 | Boswell et al. |
| 2018/0360698 | A1 | 12/2018 | Boswell |
| 2018/0369079 | A1 | 12/2018 | Boswell |

FOREIGN PATENT DOCUMENTS

| | | |
|---|---|---|
| EP | 2316436 A1 | 5/2011 |
| EP | 2316438 A1 | 5/2011 |
| EP | 2559425 A1 | 2/2013 |
| GB | 2221620 B | 9/1991 |
| JP | S5052044 U | 5/1975 |
| JP | 2002249422 A | 9/2002 |
| JP | 2004051516 A | 2/2004 |
| JP | 2006021789 | 1/2006 |
| JP | 2011178693 | 2/2010 |
| KR | 20080014461 A | 2/2008 |
| KR | 100871282 B1 | 11/2008 |
| WO | WO9216202 A1 | 10/1992 |
| WO | WO9528136 A1 | 10/1995 |
| WO | WO1996014822 | 5/1996 |
| WO | WO97032567 A1 | 9/1997 |
| WO | WO9748387 A1 | 12/1997 |
| WO | WO9926572 A1 | 6/1999 |
| WO | WO2000030694 | 6/2000 |
| WO | WO0075220 A1 | 12/2000 |
| WO | WO2001001816 | 1/2001 |
| WO | WO2001001951 | 1/2001 |
| WO | WO2001001952 | 1/2001 |
| WO | WO2001078678 | 10/2001 |
| WO | WO03063817 A1 | 8/2003 |
| WO | WO03084579 A1 | 10/2003 |
| WO | WO2004077990 A1 | 9/2004 |
| WO | WO2004078122 A2 | 9/2004 |
| WO | WO2006062740 A3 | 8/2006 |
| WO | WO2008071310 A1 | 6/2008 |
| WO | WO2009055048 A1 | 4/2009 |
| WO | WO2010057189 A1 | 5/2010 |
| WO | WO2014079459 A1 | 5/2014 |

OTHER PUBLICATIONS

All Office Actions, U.S. Appl. No. 16/015,644.
All Office Actions, U.S. Appl. No. 14/918,989.
All Office Actions, U.S. Appl. No. 15/296,630, case No. 14080MQL.
All Office Actions, U.S. Appl. No. 15/296,713, case No. 14081M.
All Office Actions, U.S. Appl. No. 15/296,736, case No. 14082MQL.
All Office Actions, U.S. Appl. No. 15/839,287, case No. 14082MCQL.
All Office Actions, U.S. Appl. No. 15/843,812, case No. 14650M.
All Office Actions, U.S. Appl. No. 15/843,866, case No. 14651M.
All Office Actions, U.S. Appl. No. 15/865,384, case No. 14502M.
All Office Actions, U.S. Appl. No. 15/865,402, case No. 14502M2.
All Office Actions, U.S. Appl. No. 15/296,768, case No. 14082M2QL.
How to Make Water-in-Oil (W/O) Emulsions, Making Cosmetics Inc., http://www.makingcosmetics.com/articles/27-how-to-make-water-in-oil-emulsions.pdf, retrieved online on Mar. 20, 2014.
International Search Report and Written Opinion of the International Searching Authority, PCT/US019/022838, dated Jun. 26, 2019, 11 pages.
International Search Report and Written Opinion of the International Searching Authority, PCT/US2015/056667, dated Dec. 21, 2015, 13 pages.
International Search Report and Written Opinion of the International Searching Authority, PCT/US2015/056670, dated Dec. 21, 2015, 16 pages.
International Search Report and Written Opinion of the International Searching Authority, PCT/US2016/057470, dated Dec. 20, 2016, 10 pages.
International Search Report and Written Opinion of the International Searching Authority, PCT/US2016/057472, dated Dec. 23, 2016, 12 pages.
International Search Report and Written Opinion of the International Searching Authority, PCT/US2016/057476, dated Dec. 20, 2016, 10 pages.
International Search Report and Written Opinion of the International Searching Authority, PCT/US2018/012869, dated Apr. 30, 2018, 12 pages.
International Search Report and Written Opinion of the International Searching Authority, PCT/US2018/012870, dated Apr. 30, 2018, 13 pages.
International Search Report and Written Opinion of the International Searching Authority, PCT/US2018/012871, dated May 28, 2018, 10 pages.
International Search Report and Written Opinion of the International Searching Authority, PCT/US2018/012873, dated May 28, 2018, 10 pages.
International Search Report and Written Opinion of the International Searching Authority, PCT/US2018/038896, dated Oct. 5, 2018, 10 pages.
Ovington, Liza G., Advances in Wound Dressings, Clinics in Dermatology, 2007, vol. 25, pp. 33-38.
PCT International Search Report, dated Dec. 20, 2016, 10 pages.
Schut, J., Foamed Films Find New Niches, Plastics Technology, Jan. 2002 Issue, 5 pages.
www.gnpd.com Record ID: 1119887, Day Out First Aid Kit, Savlon, Jun. 2009.

\* cited by examiner

METHOD OF MAKING A BARRIER PATCH WITH SOLUBLE FILM

TECHNICAL FIELD

The present invention relates to a method of making a multi-layer beauty care product comprising a barrier patch and a soluble film wherein the soluble film comprises a skin active agent for improving skin appearance.

BACKGROUND

The benefits of using a patch or mask device comprising skin active agents to cosmetically treat the skin, have been recognized in the art. A variety of cosmetic patches are commercially marketed and are useful for the delivery of skin actives. Patches have also been described in the literature and marketed in the medical field as a useful means for the transdermal administration of drugs.

Certain beauty care patch systems comprise an active reservoir in which the active is present in solid, liquid or dissolved form and a layer of pressure-sensitive adhesive by which the system can be brought into close contact with the skin. These systems are limited when the active does not diffuse through the adhesive layer, when a chemical reaction occurs between the active and the adhesive, when the active is insoluble or only poorly soluble in the adhesive or when the manufacturing process is complex.

A variety of manufacturing methods are used to assemble these patch products including printing methods. However, currently available printing methods for patch products suffer drawbacks. For example, current methods may result in inadequate adhesion of the printed fluids or films to the transfer substrate that is used and thus de-wetting may occur. It is also important to print an adequate quantity of active containing fluids to ensure adequate levels of active ingredients are provided in each unit dose of the product. If multiple printing stations are needed to provide adequate doses of active, this increases cost and complexity of the manufacturing process. If low viscosity fluids having excessive water are used, multiple drying stations are needed which again, adds cost and complexity to the process. From a manufacturing complexity stand point, it is desirable to minimize the use of multiple drying and printing stations. When a transfer substrate is used to transfer the active containing film to an adhesive or backing layer, current methods may also leave excessive residue on the transfer substrate.

Thus, it would be desirable to provide an improved process for making a multi-layer beauty care product. It would also be desirable to use a transfer substrate that enables improved transfer of a water-soluble film/fluid to a pressure sensitive adhesive such that any problems with de-wetting is minimized.

SUMMARY

The present disclosure relates to incorporating at least one soluble film zone into a beauty care product. In one aspect, a method of making a multi-layer beauty care product for applying a skin active agent to the skin is provided. The method involves preparing a transfer substrate having a first surface; preparing a water-soluble fluid by dispersing a cosmetic composition comprising an effective amount of a skin active agent into a water-soluble film forming polymer and mixing until homogeneous to achieve a viscosity from about 25,000 cP to about 85,000 cP. In some instances, the method further involves forming a multi-layer product by providing an image carrier screen having an upper side and a lower side and a plurality of channels and having a mesh or pore size corresponding to about 40 mesh to about 500 mesh; positioning the transfer substrate under the lower side of the image carrier screen with the first surface of the transfer substrate in contact the lower side of the image carrier screen; applying the fluid to the upper side of the image carrier screen whereby the transfer substrate is coated with the fluid through the channels of the image carrier screen; removing the image carrier screen; drying the fluid to a film; preparing a backing layer having a first surface and a second surface and a WVTR from about 1 $g/m^2/24$ h to about 500 $g/m^2/24$ h; applying a pressure sensitive adhesive to the first surface of the backing layer; and separating the dry, water-soluble film from the transfer substrate by contacting the pressure sensitive adhesive side of the backing layer to the dry, water-soluble film and applying a sufficient separation force.

DETAILED DESCRIPTION

Figure 1:
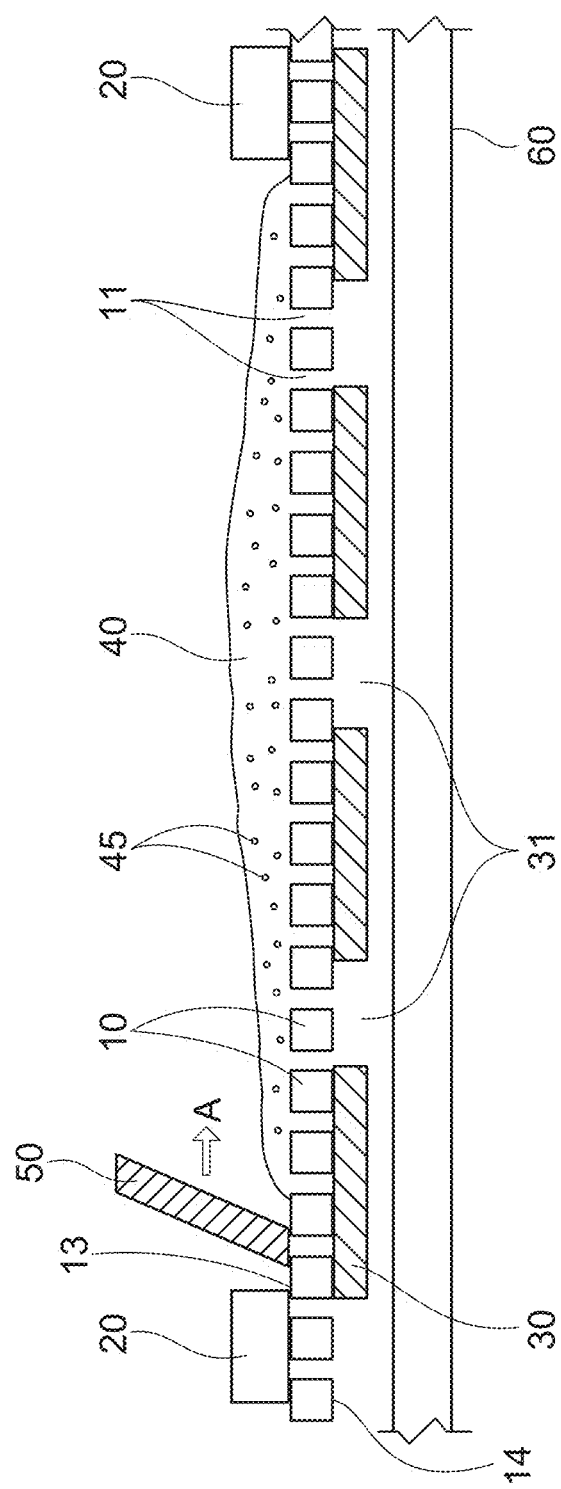
FIG. 1 illustrates a cross-sectional view of a method of forming a pattern of water-soluble fluid using an image earner screen mounted to a frame, the image earner screen having mesh and a pattern film attached thereto.

The methods and associated products described herein provide an improved process for making a multi-layer beauty care product via a transfer substrate that enables improved transfer of a water-soluble film/fluid to a pressure sensitive adhesive such that any problems with de-wetting is minimized. In addition, the use of the transfer substrate advantageously avoids the need to handle the film when wet or dry. A product is provided where the peel force of the water-soluble film/fluid from the transfer substrate is less than the peel force of the water-soluble fluid/film in contact with the pressure sensitive adhesive. Minimal residue on the transfer substrate thus remains after the transfer of the active containing film to the adhesive is complete. Proper transfer also minimizes the mixing of the active and the adhesive to avoid any negative interactions between the adhesive and active. The method also improves the balance between the channel or mesh size of the image carrier screen and the viscosity of the water-soluble fluid used to achieve the proper coating thickness, coating weight and/or adequate levels of the active agents in the product.

All percentages and ratios used herein are by weight of the total composition. All numeric ranges are inclusive of narrower ranges; delineated upper and lower range limits are interchangeable to create further ranges not explicitly delineated. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Molecular weight" means the weight average molecular weight unless otherwise stated. Molecular weight is measured using industry standard method, gel permeation chromatography ("GPC"). "Apply" or "application" means to apply or spread the compositions onto a substrate such as the human skin surface or epidermis.

"Dermatologically acceptable" means that the compositions or components thereof so described are suitable for use in contact with mammalian keratinous tissue without undue toxicity, incompatibility, instability, allergic response, and the like.

"Facial skin surface" means one or more of forehead, periorbital, cheek, perioral, chin, and nose skin surfaces. While facial skin surfaces are of concern and are exemplified herein, other skin surfaces may be treated with the compositions and methods of the present invention, for example, surfaces typically not covered by clothing such as facial skin surfaces, hand and arm skin surfaces, foot and leg skin surfaces, and neck and chest skin surfaces (e.g., décolletage).

"Healthy skin" means that the physical barrier function of the epidermis and the dermis is maintained intact for example, the stratum corneum of skin is intact, and is not physically disrupted, removed, subject to reduction, wounded, altered or ablated using mechanical, optical, or thermal means.

"Keratinous tissue" means keratin-containing layers disposed as the outermost protective covering of mammals (e.g., humans, dogs, cats, etc.) which includes, but is not limited to, skin, mucosa, lips, hair, toenails, fingernails, cuticles, hooves, etc.

"Topically applied" means to apply (e.g., spread, spray) the compositions of the present invention onto the surface of the keratinous tissue.

"Effective amount" means an amount of a compound or composition sufficient to significantly induce a positive keratinous tissue benefit, including independently or in combination with other benefits disclosed herein. This means that the content and/or concentration of agent in the formulation is sufficient that when the formulation is applied with normal frequency and in a normal amount, the formulation can result in the treatment of one or more undesired keratinous tissue conditions (e.g., skin wrinkles). For instance, the amount can be an amount sufficient to inhibit or enhance some biochemical function occurring within the keratinous tissue. This amount of the skin care agent may vary depending upon the type of product, the type of keratinous tissue condition to be addressed, and the like.

"Safe and effective amount" means an amount of a compound or composition sufficient to significantly induce a positive benefit, preferably a positive keratinous tissue appearance, including independently or in combinations with the benefits disclosed herein, but low enough to avoid serious side effects, i.e., to provide a reasonable benefit to risk ratio, within the scope of sound judgment of the skilled artisan.

"Water impermeable" means materials or objects through which water in its liquid state does not pass.

"Substantially free of" mean an amount of a material that is less than 2%, 1%, 0.5%, 0.25%, 0.1%, 0.05%, 0.01%, or 0.001% by weight, of product, the barrier patch, the water-soluble film zone or fluid, the water-soluble film forming polymer, or the backing layer of the barrier patch. "Free of" refers to no detectable amount of the stated ingredient or thing.

"Nonwoven" means a porous, fibrous material made from continuous (long) filaments (fibers) and/or discontinuous (short) filaments (fibers) by processes such as, for example, spun bonding, melt blowing, carding, and the like. Nonwoven webs do not have a woven or knitted filament pattern.

DISCUSSION OF THE FIGURES

Exemplary aspects of the method are shown in FIGS. 1, 2, 3 and 4. Aspects will now be described more fully with reference to the accompanying drawings, in which exemplary aspects of the invention are shown.

Figure 2:
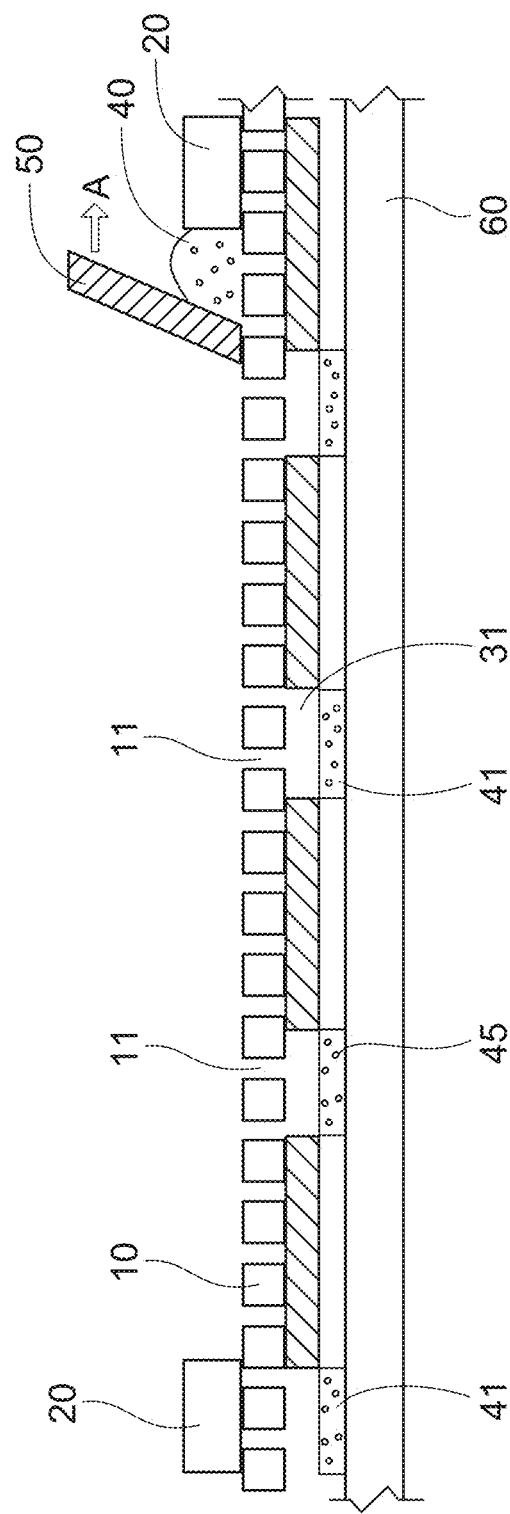
FIG. 2 illustrates a cross-sectional view of transferring the water-soluble fluid to the transfer substrate.

FIGS. 1 and 2 illustrate a cross-sectional view a method of forming a pattern of water-soluble fluid using an image carrier screen 10. The image carrier screen may be tensioned and mounted to a frame 20. A water-soluble fluid 40 comprising an active agent 45 is applied to an image carrier screen 10. The image carrier screen 10 has channels 11 therethrough. The image carrier screen 10 also has an upper side 13 and a lower side 14. A pattern film 30 is connected or attached to the lower side 14 of the image carrier screen 10. The pattern film 30 is attached to the image carrier screen 10 in a discontinuous manner such that gaps are formed between the pattern film 30 to create a plurality of openings 31. Below the pattern film 30 and the image carrier screen 10 is a transfer substrate 60. FIG. 1 also includes a squeegee 50 that aids in the transfer of the water-soluble fluid 40 through the channels 11 of the of the image carrier screen 10 and through the openings 31 of the pattern film 30. The fluid is squeegeed onto the transfer substrate 60 through the mesh openings or channels 11 of the image carrier screen 10 that are not blocked by the pattern film 30.

As used herein an image carrier screen may include a screen with a particular mesh size or pore size such as mesh screen size of from about 40 mesh to about 500 mesh, preferably from about 175 mesh to about 350 mesh or from about 200 mesh to about 300 mesh. The image carrier screen may include rotary screens or flat-bed screens.

The image carrier screen may also be a self-supporting material such as a polymeric film, e.g. a perforated silicone sheet, with a pore size or channel size that is roughly equivalent to the channel size of a mesh for the image carrier screen as discussed herein.

Mesh size, as used herein, means the number of threads of mesh that cross per square inch. For instance, a 110-mesh screen has 110 threads crossing per square inch. In an aspect, the screen may be of a mesh count such as a fine, 400-500 mesh, with a thread diameter of 25.4 microns to a coarse 40 mesh and having a thread diameter of as much as 203.2 microns. The chosen screen size will depend upon the particular application. In an aspect, an image carrier screen 10 is provided, having an upper side 13 and a lower side 14 and a plurality of channels 11 and having a mesh or pore size corresponding to about 40 mesh to about 500 mesh, preferably from about 175 mesh to about 350 mesh or from about 200 mesh to about 300 mesh, wherein the thread size diameter may vary from about 25.4 microns to about 203.2 microns.

The image carrier screen thickness is also an important aspect herein since the amount of water-soluble fluid deposited on the transfer substrate is to some extent dependent on the thickness. The image carrier screen may have a pattern film. In one aspect, the total thickness of the image carrier screen including the pattern film equals the mesh thread diameter plus the thickness of the pattern film, which may be from about 40 microns to about 100 microns, preferably from about 50 microns to about 70 microns, more preferably from about 55 microns to about 65 microns.

In an aspect for the image carrier screen 10 to be effective, it is mounted on frame 20 under tension, for example in both the machine direction (MD) and the cross-machine direction (CD) direction. Referring to FIGS. 1 and 2, the image carrier screen 10 may be tensioned via the frame 20, in the direction of arrow A and a cross direction B (not shown) to direction A.

The frame 20 may be made of a variety of materials, such as wood or aluminum, depending on the sophistication of the machine. A tensiometer may be used to measure the tension of the screen in Newtons per centimeter (N/cm).

In an aspect, the image carrier screen 10 is a metal screen such as the rigid woven metal screen as particularly disclosed in U.S. Pat. No. 3,482,300, or the all-metal self-supporting screen disclosed in U.S. Pat. No. 3,759,799. One of the advantages of such screens is that they can be made in a variety of screen mesh counts such as from a fine screen of about 400 mesh to a coarse screen of about 40 mesh, or from about 150 mesh to about 300 mesh, having thread diameters of for example, 21.8 microns to 25.4 microns, in order to satisfy a variety of screen printing applications. With respect to making a cylindrical printing screen from metal woven mesh screen material of the type disclosed in U.S. Pat. No. 3,482,300 and U.S. Pat. No. 3,759,799, a screen section is cut and cylindrically shaped with edges overlapped and usually bonded together with adhesive such as an epoxy. The overlapped seam can also be welded by a resistance welder, but in either case, the overlapped seam defines a rough area along the screen over which the squeegee of the printing press has to jump on each revolution of the screen. The cylindrical printing screen may then be used in a flat-bed, cylinder, and/or rotary process. Rotary screen printing presses are illustrated in U.S. Pat. No. 3,155,034. Such presses may utilize a printing screen that is cylindrical in form such as those illustrated in U.S. Pat. Nos. 3,482,300; 3,696,741; 3,759,799; and 3,759,800.

More particularly, the screen material may be Phosphor bronze or stainless steel of the "taffeta" weave type and screen made of stainless steel with nickel. The "taffeta" weave relates to a screen material where wires extend normal to each other and cross over and under each other so that wires extending in one direction intersect and engage wires extending normal thereto, and thereby define openings of a size to the screen.

In an aspect, synthetic threads may be used for the image carrier screen, in the method herein. The synthetic threads may be made of polyester, nylon, stainless steel and combinations thereof.

Also shown in FIGS. 1 and 2 is a transfer substrate 60 which may be mounted on a support (not shown). The transfer substrate 60 may be a flexible, self-supporting plastic or polymeric film material. In an aspect, the transfer substrate may be a biaxially-oriented polyester film, polyester film, etc. Some examples of polyester films include MYLAR and MELINEX, which are generally known as BoPET or biaxially-oriented polyethylene terephthalate and are available from Dupont.

The pattern film 30 has a plurality of openings 31. The pattern film 30 may be disposed between the image carrier screen 10 and the transfer substrate 60. A pattern (not shown) of the water-soluble fluid 40 is created on the transfer substrate 60, as the water-soluble fluid 40 is transferred through the channels 11 and through the openings 31 in the patterned film 30.

The pattern film 30 is generally applied to the image carrier screen (e.g. mesh screen) via processes known in the art. For example, the pattern film 30 may be coated on the image carrier screen. In an aspect, a stencil is formed by blocking off parts of the image carrier screen in the negative image of the design/pattern of the water-soluble fluid to be printed on the transfer substrate. Openings are where the water-soluble fluid will appear on the backing layer or on the adhesive surface. In an aspect, an image carrier screen is selected and then it is coated with an emulsion and dried. Once dry, it is then possible to burn/expose the print into the screen. For example, an overlay is placed over the screen, and then exposed with a light source containing ultraviolet light in the 350-420 nanometer spectrum. Then the screen is washed off thoroughly. The areas of emulsion that were not exposed to light dissolve and wash away, leaving a negative stencil of the pattern film 30 on the screen.

Referring to FIG. 2, the water-soluble fluid 40 is transferred onto the transfer substrate 60 by moving a squeegee 50 across the image carrier screen 10, in the direction of the arrow A, to form fluid pattern 41. The squeegee 50 movement transfers the water-soluble fluid 40 through the channels 11 of the image carrier screen 10 and through the openings 31 of the pattern film 30. The water-soluble fluid 40 is squeegeed onto the transfer substrate 60 through the channels 11 of the image carrier screen 10 that are not blocked by the pattern film 30. To increase uniformity of the transferred fluid patterns 41, the operations described with reference to FIG. 2 may be repeated. The amount of remaining water-soluble fluid 40 on the image carrier screen 10, when peeling off the image carrier screen 10 after the transferring operation is complete, may be reduced by proper tensioning of the image carrier screen 10, as mentioned herein. This may be accomplished by mounting the image carrier screen 10 to the frame 20 and keeping the tension uniformly distributed over the channels 11 and/or the openings 31 of the pattern film 30, during the transfer operation. This increases the volume of the water-soluble fluid 40 passing through the image carrier screen 10.

According to an aspect, a pattern direction of the pattern film 30 may be parallel to the first tensioning direction which may be the arrow A direction, and a fluid pattern 41 may be transferred to the transfer substrate 60 while moving the squeegee 50 along this first direction (see FIGS. 1 and 2). According to an aspect, the fluid patterns 41 of the pattern film 30 may extend diagonally between opposing sides of the frame 20. According to an aspect, the fluid patterns 41 of the pattern film 30 may be perpendicular to opposing sides of the frame 20.

Figure 3A:
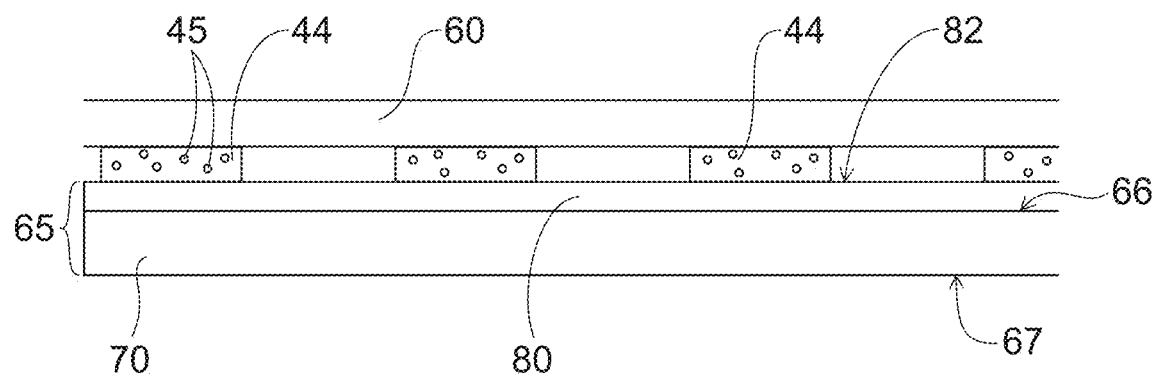
FIG. 3A illustrates a cross-section view of applying the water-soluble fluid after it has dried to a water-soluble film, to the pressure sensitive adhesive.
Figure 3B:
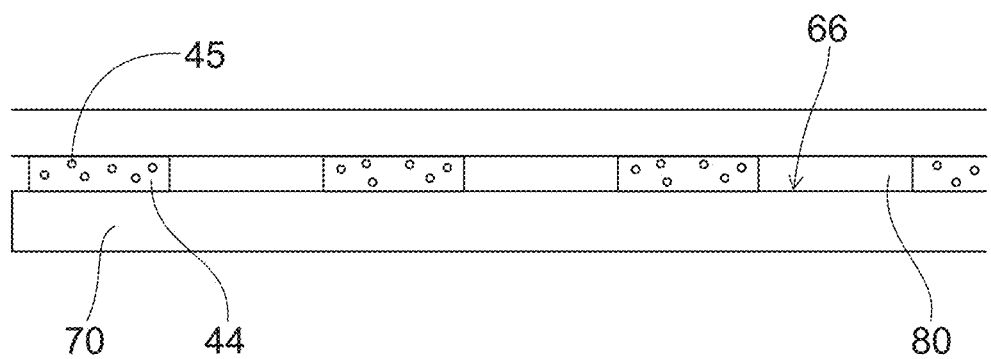
FIG. 3B illustrates an alternative cross-section view of applying the water-soluble fluid after it has dried, to the pressure sensitive adhesive.

FIGS. 3A and 3B illustrate a cross-section view of applying the water-soluble fluid 40, after drying to form a dry water-soluble film 44, to the pressure sensitive adhesive 80 or the first surface 66 of the backing layer 70. In FIG. 3A, the barrier layer 65 comprises a pressure sensitive adhesive 80 and a backing layer 70. The backing layer 70 has a first surface 66 and a second surface 67. The dry water-soluble film 44 is attached by contacting it with either the first surface 66 of the backing layer 70 or contacting it with the pressure sensitive adhesive 80. In FIG. 3A, the dry water-soluble film 44 is contacted with a continuous layer or coating of the pressure sensitive adhesive 80 on the pressure sensitive adhesive side 82 of the barrier layer 65. The barrier layer 65 has a pressure sensitive adhesive side 82.

FIG. 3B illustrates a backing layer 70 and a discontinuous layer or coating of the pressure sensitive 80. Here the pressure sensitive adhesive 80 is configured on the first surface 66 of the backing layer 70 in a discontinuous pattern. The discontinuous pattern has openings or gaps in the pressure sensitive adhesive 80 pattern. The pressure sensitive adhesive 80 may constitute islands surrounded by continuous gaps or may constitute a series of stripes of pressure sensitive adhesive 80 with alternating stripes/openings without any pressure sensitive adhesive 80. Thus in FIG. 3B the dry water-soluble film 44 is contacted and attached to the first surface 66 of the backing layer 70 and is positioned in between the openings of the discontinuous pressure sensitive adhesive 80 pattern. Thus, the pressure sensitive adhesive 80 may be applied to the backing layer 70 in any number of patterns (not shown). For example, the continuous coating or layers or discontinuous layers or coatings of the pressure sensitive adhesive 80 may be used, as discussed herein. Thus, in FIG. 3B, both the pressure sensitive adhesive 80 and the dry water-soluble film 44 comprise discontinuous patterns.

Figure 4:
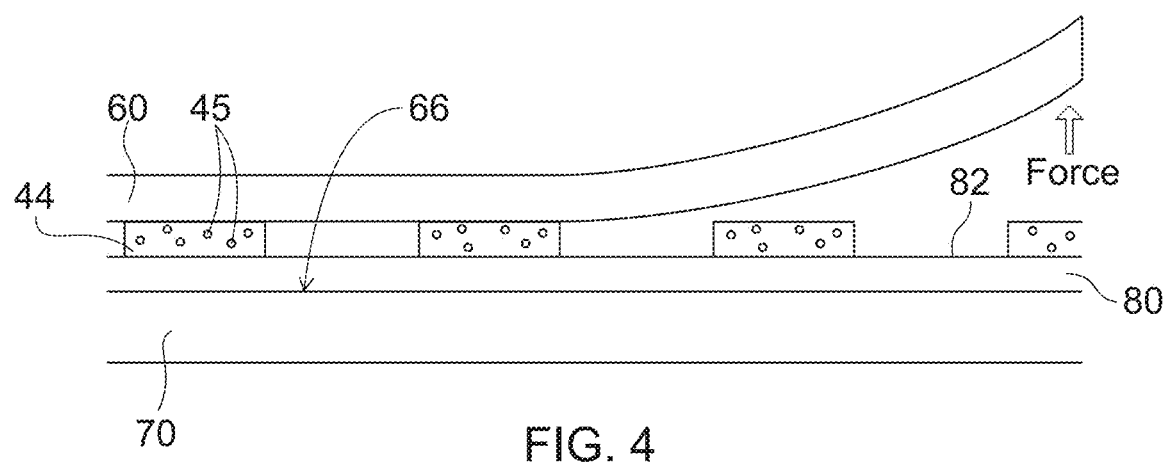
FIG. 4 illustrates an alternative view of a cross-section view of the water-soluble fluid after it has dried to a water-soluble film, to the backing layer.

In FIG. 4, the dry water-soluble film 44 is separated from the transfer substrate 60 by first contacting the dry water-soluble film 44 to the pressure sensitive adhesive side 82 of the barrier layer. Then a force is applied to separate the dry water-soluble film 44 from the transfer substrate 60, to form a patch product having a backing layer 70, a pressure sensitive adhesive 80 and a dry water-soluble film 44.

The patch product may further comprise a release layer (not shown).

In an aspect, a proper balance of the viscosity of the water-soluble fluid with the mesh size or channel size of the image carrier screen is desired. This proper balance avoids overloading the fluid through the channels and spreading out to far on the transfer substrate which may cause alter the amount of active agent concentration or may cause the pattern of the wet or dry water-soluble film to be indistinct (e.g. as the fluid bleeds).

In an aspect, the water-soluble fluid has a viscosity of 25,000 cP to about 85,000 cP, preferably from about 28,000 cP to about 60,000 cP, or more preferably from about 30,000 cP to about 50,000 cP, e.g. and this viscosity may be used with an image carrier screen having a mesh size of 175 mesh to about 250 mesh.

FIGS. 5 to 10 show the transfer of printed films using different pressure sensitive adhesives and different backing layers.

Figure 5:
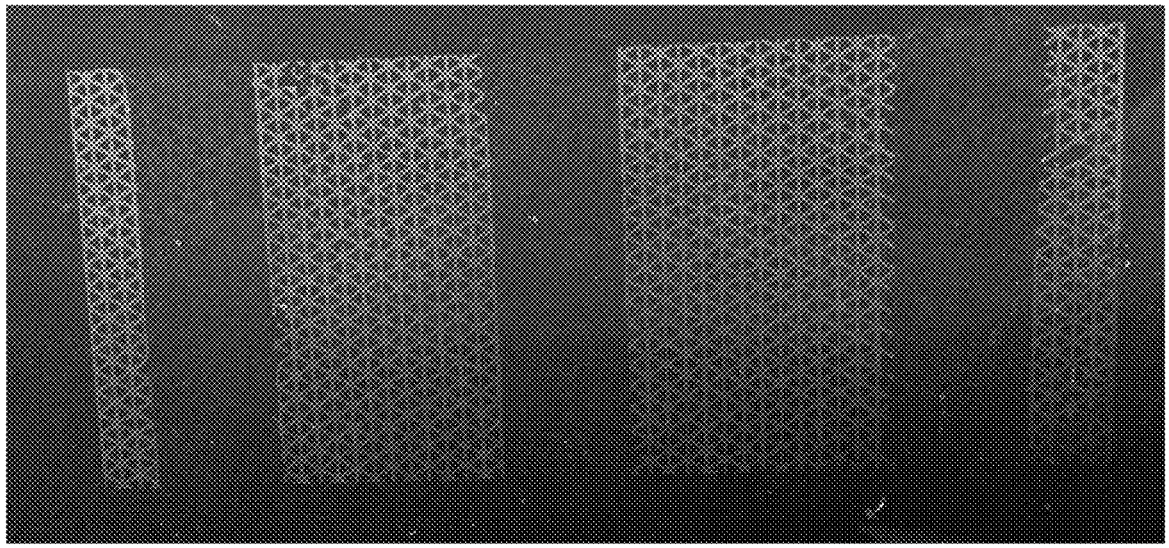
FIG. 5 is an image of a water-soluble film coated on a transfer substrate where portions of the film have been removed by contacting it with a backing layer with an adhesive.

FIG. 5 shows a dry water-soluble film (shown as a patterned film) comprising a similar composition as in the Example herein. The water-soluble film is coated on a transfer substrate comprising PET such a MYLAR, also shown. Three 1.9 cm strips of 3M 1525L, which comprises an adhesive layer, are used as a barrier layer. These strips are applied via the adhesive side of 3M 1525L, to the soluble film. The backing layer is then stripped away. As can be seen the soluble film is removed from the transfer substrate leaving clean and clear lines around the edges. Clear areas are where the soluble film has transferred to the 1.9 cm samples of adhesive/barrier/backing layer. Clean, clear lines are indicative of an effective transfer process. The peel force used in FIG. 5 is 554 g/2.54 cm.

Figure 6:
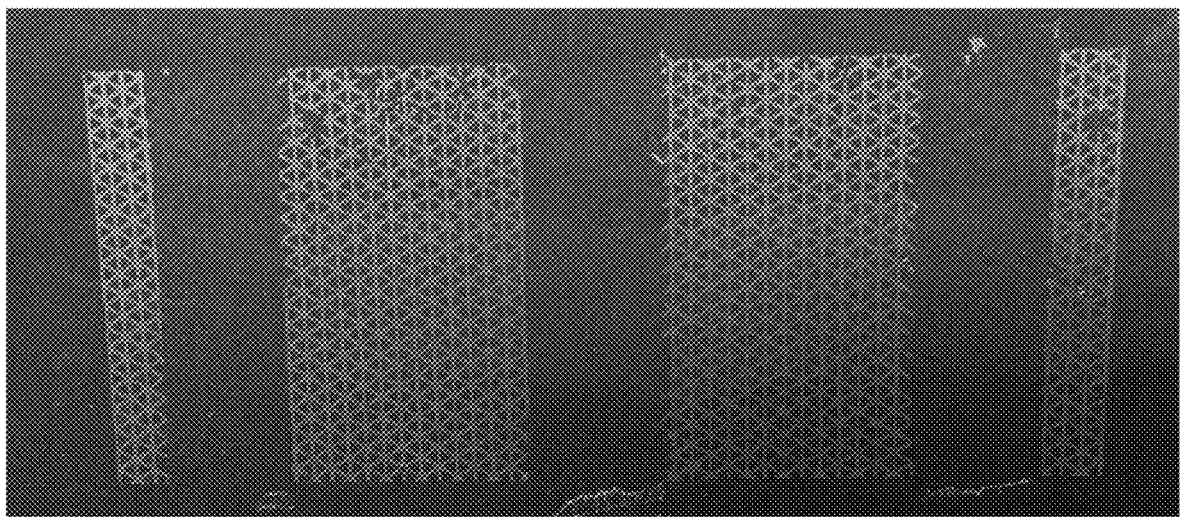
FIG. 6 is an image of a water-soluble film coated on a transfer substrate where portions of the film have been removed by contacting it with a backing layer with an adhesive.

FIG. 6 shows a dry water-soluble film (shown as a patterned film) comprising a similar composition as in the Example herein. The water-soluble film is coated on a transfer substrate comprising PET such as MYLAR brand PET, also shown. Three 1.9 cm strips of an oil gel pressure sensitive adhesive, Henkel Technomelt PSM 539B Derma-Tak, (2 mil coating) on a 100 grams/m$^2$ (gsm) foamed ethylene vinyl acetate backing layer were evaluated. These strips are applied via the adhesive side of this backing layer, to the soluble film. The backing layer is then stripped away. As can be seen the soluble film is removed from the transfer substrate leaving clean and clear lines around the edges. Clear areas are where the soluble film has transferred to the 1.9 cm samples of adhesive/barrier/backing layer. Clean, clear lines are indicative of an effective transfer process. The peel force for FIG. 6 is 538 g/2.54 cm.

Figure 7:
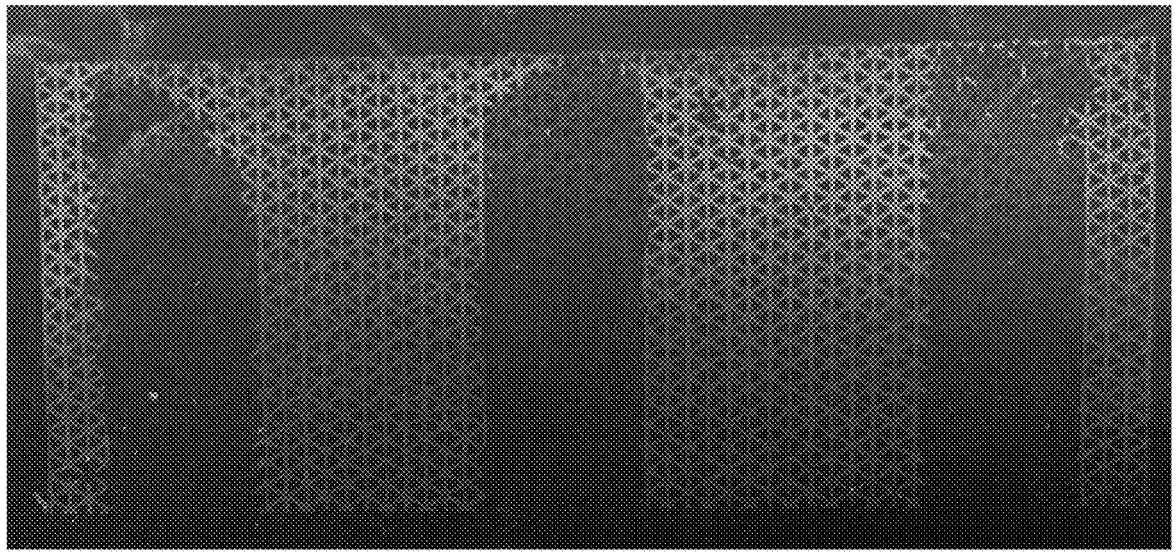
FIG. 7 is an image of a water-soluble film coated on a transfer substrate where portions of the film have been removed by contacting it with a backing layer with an adhesive.

FIG. 7 shows a dry water-soluble film (shown as a patterned film) comprising a similar composition as in the Example herein. The water-soluble film is coated on a transfer substrate comprising PET such a MYLAR, also shown. Three 1.9 cm strips of a 3M 2476P which comprises a silicone adhesive and a white polyester spunlace nonwoven/film laminate, available from 3M, were evaluated. These strips are applied, via the adhesive side of this backing layer, to the soluble film. The backing layer is then stripped away. As can be seen, most of the soluble film is removed from the transfer substrate. Significant areas of soluble film around the top, however, did not transfer. Jagged edges also exist, indicative of a less effective transfer process. The peel force for FIG. 8 is 166 g/2.54 cm.

Figure 8:
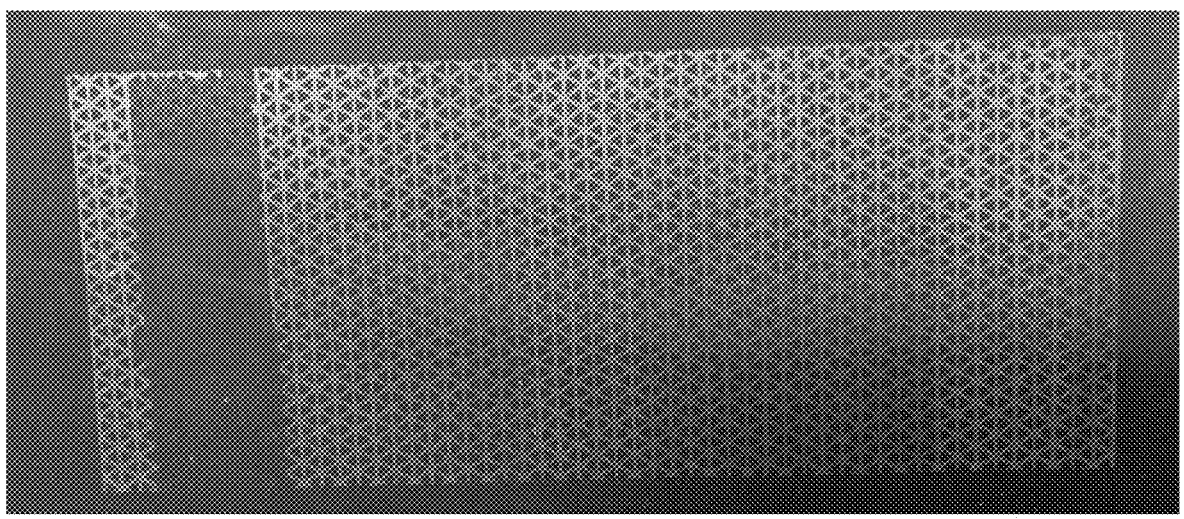
FIG. 8 is an image of a water-soluble film coated on a transfer substrate where portions of the film have been removed by contacting it with a backing layer with an adhesive.

FIG. 8 shows a dry water-soluble film (shown as a patterned film) comprising a similar composition as in the Example herein. The water-soluble film is coated on a transfer substrate comprising PET. Three 1.9 cm strips of a silicone adhesive 267 with a coat weight of 250 gsm and a polyurethane backing layer (provided by Marian Inc.) were evaluated. These strips are applied, via the adhesive side of this backing layer, to the soluble film. The backing layer is then stripped away. As can be seen, the majority of the soluble film is removed from the transfer substrate for one of the strips but very little if any soluble film is removed at all from the other 2 strips. Jagged edges also exist for the first strip. This is indicative of a less effective and inconsistent transfer process. The peel force for FIG. 8 is 28 g/2.54 cm.

Figure 9:
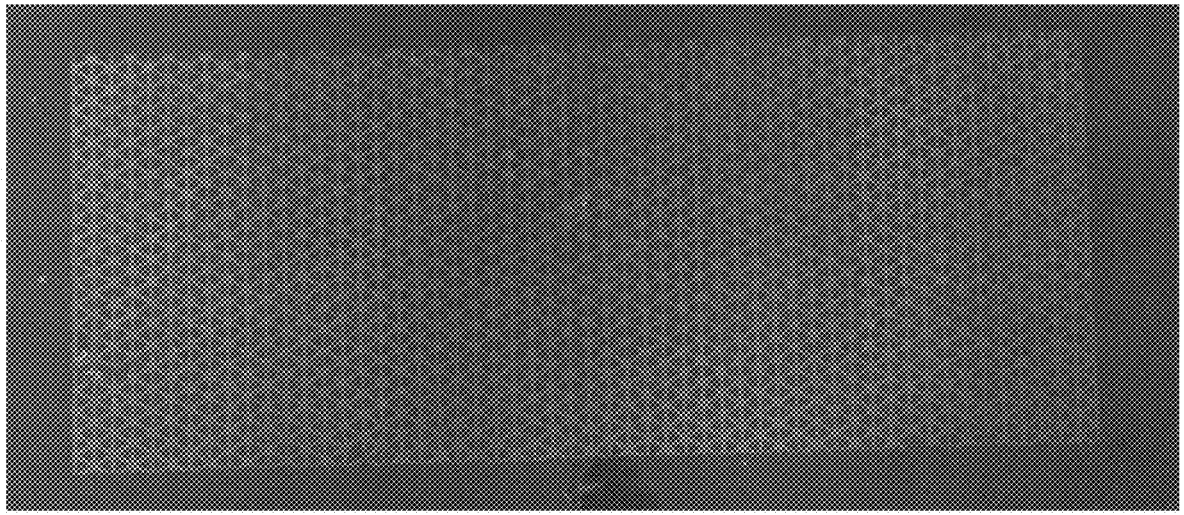
FIG. 9 is an image of a water-soluble film coated on a transfer substrate where only minimal portions of the film have been removed by contacting it with a backing layer with an adhesive.

FIG. 9 shows a dry water-soluble film (shown as a patterned film) comprising a similar composition as in the Example herein. The water-soluble film is coated on a transfer substrate comprising PET such as Mylar, also shown. Three 2.03 cm samples of Gentac Fixation tape, comprising a silicone adhesive and made by Medline Industries, were evaluated. These strips are applied via the adhesive side of the backing layer, to the soluble film. The backing layer is then stripped away. As can be seen, the soluble film was not removed from the transfer substrate. This is indicative of an ineffective transfer process. The peel force for FIG. 9 is 26.8 g/2.54 cm.

Figure 10:
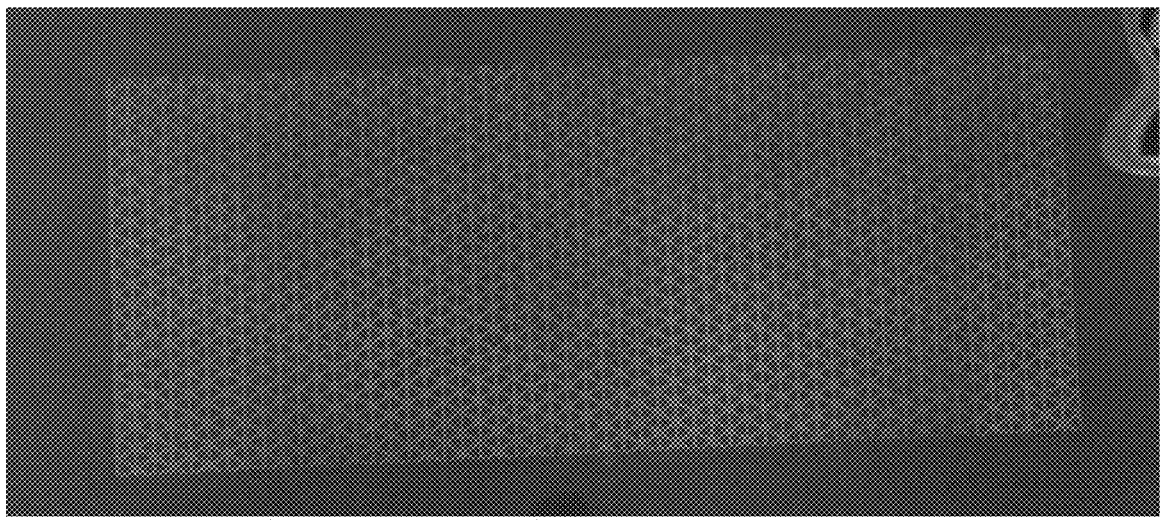
FIG. 10 is an image of a water-soluble film coated on a transfer substrate where only minimal portions of the film have been removed by contacting it with a backing layer with an adhesive.

FIG. 10 shows a dry water-soluble film (shown as a patterned film) comprising a similar composition as in the Example herein. The water-soluble film is coated on a transfer substrate comprising PET such as MYLAR, also shown. Three 1.9 cm samples of HYDRO COOL FIRMING NECK GELS available from SKYN Iceland comprising a hydrogel adhesive were evaluated. These strips are applied, via the adhesive side of the backing layer, to the soluble film. The backing layer is then stripped away. As can be seen, the soluble film was not removed from the transfer substrate. This is indicative of an ineffective transfer process. The peel force for FIG. 10 is 6.45 g/2.54 cm.

Water-Soluble Fluid for Water-Soluble Film Zone

The water-soluble fluid, for making a water-soluble film zone, comprises a water-soluble film forming polymer and a cosmetic composition comprising an effective amount of a skin active agent. The water-soluble film forming polymer forms a water-soluble film. As used herein "water-soluble film" means a film that dissolves according to the dissolution method herein.

In an aspect, the water-soluble fluid or film zone comprises from about 30% to about 99% or from about 40% to about 90%, more preferably from about 50% to about 75% of a water-soluble film forming polymer.

As used herein a "low water environment" of the skin, means the humidity or moisture provided, under occlusion, from the inner skin layer(s) of healthy skin to the surface of the skin via the pores in the skin. This may comprise components of sweat, sebum or oil. For example, a low water environment includes the humidity build up on the skin when the product herein is applied to the skin for about 1 to 8 hours or longer, the product comprising a backing layer having a low breathability (e.g. low WVTR, the proper thickness, etc.), as provided herein.

The water-soluble film zone or product is thus capable of increasing in weight as the buildup of water/humidity occurs under the product when applied to the skin. As this transformation occurs, the skin active agent may be released from the product to the skin of the user and be absorbed into the skin to have the intended effect.

The water-soluble film zone or product is also capable of decreasing in modulus as the buildup of water/humidity occurs under the product when applied to the skin. Thus, the product or water-soluble film zone provides a "dynamic" modulus where the modulus decreases during wear to improve the comfort of the product. As this transformation occurs, the skin active agent may be released from the product to the skin to have the intended effect. The water-soluble film zone or product is also capable of decreasing opacity as the buildup of water/humidity occurs under the product when applied to the skin, which may serve as an indication that the product is working as intended.

Without being bound by theory, the soluble film zone or soluble film dissolves, disintegrates, and/or loses its physical integrity when exposed to low water environments. As the water-soluble film zone or water-soluble film softens and/or dissolves, the active is released. The soluble film zone or water-soluble film, prior to exposure to a low water environment, is a dry film comprising a water-soluble polymer.

In an aspect, the soluble film zone comprises a skin active agent. In an aspect, the skin active agent is only minimally released, if at all, from the soluble film zone in the dry form prior to use and/or prior to exposure to the low water environment and/or in the absence of moisture or water. When a low level of water, contacts the soluble film zone, softening, dissolution or breakdown, begins to occur, thereby enabling the skin active to migrate out of the soluble film zone and/or penetrate to the skin surface or into the skin. In an aspect in the presence of water, skin active agents present in the soluble film zones are believed to be more readily available to the skin due to the faster rates of diffusion through the soluble film zone.

In an aspect, prior to use by the consumer, the water-soluble film zone is substantially free of water or may comprise less than about 15%, 12%, or 10%, water, or comprise about 0.001% to about 15% water, or about 0.05% to about 10%, water, by weight of the soluble film zone.

Preferred water-soluble materials for the soluble film zone may be selected from polyethylene oxide polymers, polyvinyl alcohols, polyvinyl pyrrolidone, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthan and carrageenan, polyacrylates and water-soluble acrylate copolymers, polymethacrylates, methylcellulose, carboxymethylcellulose, hydroxyethyl cellulose, hydroxypropyl methylcellulose, dextrin, maltodextrin, salts thereof, and combinations thereof.

Additional water-soluble materials for the soluble film zone may be selected from polyethylene glycol, pullulan, carbohydrate polymers such as natural polysaccharide or derivates including pectin and derivatives, sodium alginate, methyl methacrylate copolymer, carboxyvinyl polymer, amylase, pectin, chitin, chitosan, levan, elsinan, collagen, gelatine, zein, gluten, soy protein isolate, whey protein isolate, casein, gums (such as guar, gum Arabic, tragacanth gum, xanthan gum, gellan sodium salt, gum ghatti, okra gum, karaya gum, locust bean gum, tara gum, quince seed gum, fenugreek seed gum, scleroglucan, psyllium seed gum, tamarind gum, oat gum, quince seed gum, rhizobium gum, biosynthetic gums, Khaya grandifolia gum, pectin, arabian, Konjac mannan, alactomannan, funoran, acetan, welan, rhamsan, furcelleran, succinoglycan, scleroglycan, and dextran, flaxseed gum), propyleneglycol, alginate, starches (such as amylose, amylopectin, modified starches, hydroxyethyl starch, carboxymethyl starch, high amylose starch, hydrooxypropylated high amylose starch, biosynthetic processed starch, starches such as rice, corn, potato, and wheat), dextrans, dextrins and maltodextrins, konjac, acemannan from aloe, carrageenans, scleraglucan, succinoglucan, larch arabinogalactan, chondroitin sulfates, hyaluronic acid, curdlan, deacetylatedkonjac, water-soluble non-gelling polypeptide or protein (such as gelatins, albumins, milk proteins, soy protein, and whey proteins), hydrocolloids (such as synthetic hydrocolloids exemplified by polyethylene-imine, hydroxyethyl cellulose, sodium carboxymethyl cellulose, carboxymethyl cellulose, hydroxypropyl cellulose, hydroxypropyl methyl cellulose, methyl cellulose, ethyl cellulose, polyacrylic acids, low molecular weight polyacrylamides and their sodium salts (carbomers), polyvinylpyrollidone, polyethylene glycols, polyethylene oxides, polyvinyl alcohols, pluronics, tetronics, and other block co-polymers, carboxyvinyl polymers, and colloidal silicon dioxide, soluble polyesters, natural seaweeds, natural seed, natural plant exudates, natural fruit extracts, glycyrrhizic acid, polyacrylic acid, vinyl polymers, cationic polymers, acrylic polymers (such as sodium polyacrylate, polyethyleacrylate and polyacrylamide), and combinations.

In an aspect, the water-soluble film zone comprises a polymer selected from the group consisting of polyethylene oxide polymer, polyvinyl alcohols, polyvinyl alcohol copolymers, starch, methylcellulose, carboxymethylcellulose sodium, hydroxyethyl cellulose, hydroxypropyl methylcellulose, hydroxypropyl cellulose, and combinations. Preferred polymers, copolymers or derivatives thereof suitable for use as water-soluble film for the soluble film zone are selected from polyethylene oxides, methylcellulose, hydroxypropyl methylcellulose, hydroxypropyl cellulose, and combinations thereof.

Preferred polymers, copolymers or derivatives thereof suitable for use as water-soluble film for the soluble film zone are selected from polyethylene oxides, and combinations thereof.

Preferred polymers, copolymers or derivatives thereof suitable for use as water-soluble film for the soluble film zone are selected from methylcelluloses, hydroxypropyl cellulose, hydroxypropyl methylcelluloses and combinations thereof.

Preferred water-soluble film forming polymers are made from polyethylene oxides such as polyethylene oxide films or polyethylene glycol, and include POLYOX, sold by the Dow Chemical Company. Polyethylene oxides include POLYOX WSR N-10 (having a molecular weight of 10,000), WSR N-80 (with a molecular weight of about 200,000), WSR N750 (with a molecular weight of about 300,000) of corresponding solubility characteristics. In an aspect, the water-soluble film comprises a polyethylene oxide having a molecular weight from about 500 to about 10,000,000 or from about 10,000 to about 1,000,000 or from about 100,000 to about 300,000 or from about 150,000 to about 250,000.

Other preferred water-soluble film forming polymers comprise plasticized methylcellulose and/or plasticized hydroxypropyl methylcellulose and/or plasticized hydroxypropylcellulose. As used herein, "plasticized" means a composition of methylcellulose or hydroxypropyl methyl cellulose or hydroxypropylcellulose, and plasticizer wherein the plasticizer is used at a level of from about 2% to about 80% or about 2% to about 60%, or from about 10% to about 50% or from about 20% to about 45% by weight of this composition.

The hydroxypropyl methylcellulose may be METHOCEL E5LV, a water-soluble cellulose ether of low viscosity available from Dow/Coloron LTD and having a viscosity is about 4.0-6.0 mPa·s, 2% in water at 20° C. Other METHOCEL grades that may be used include METHOCEL E3LV (viscosity is about 2.4-3.6 mPa·s, 2% in water at 20° C.), METHOCEL E6LV (viscosity is about 4.8-7.2 mPa·s, 2% in water at 20° C.), METHOCEL E15LV (viscosity is about 12-18 mPa·s, 2% in water at 20° C.), METHOCEL E50LV (viscosity is about 40-60 mPa·s, 2% in water at 20° C.), and METHOCEL K3LV (viscosity is about 2.4-3.6 mPa·s, 2% in water at 20° C.).

The polyethylene oxide polymers or cellulose ether may be combined with additional polymers, for example, polymers, copolymers or derivatives thereof which may be other water-soluble film forming polymers. The additional polymers may be selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthan and carrageenan, polyacrylates and water-soluble acrylate copolymers, polymethacrylates, methylcellulose, carboxymethylcellulose, hydroxyethyl cellulose, hydroxypropyl methylcellulose, dextrin, maltodextrin, salts thereof, and combinations thereof. In an aspect, the water-soluble film zone comprises polyethylene oxide polymer and an additional polymer selected from the group consisting of polyvinyl alcohols, polyvinyl alcohol copolymers, starch, methylcellulose, carboxymethylcellulose sodium, hydroxyethyl cellulose, hydroxypropyl methylcellulose and combinations.

Also suitable are mixtures of polyethylene oxide polymers having different molecular weights. The additional polymers may have weight average molecular weights of about 1,000 to 1,000,000 daltons (Da), (e.g., about 50,000 to 300,000 Da or about 20,000 to 150,000 Da). The level of polymer in the water-soluble film in the dry state may be about 20% to about 90%, or about 45% to about 85% or about 50% to about 70% by weight of the water-soluble polymer zone.

In an aspect, the water-soluble film/fluid may be a combination of polyethylene oxide such as POUYOX. WSR N-80 and methylcellulose or hydroxypropyl methylcellulose such as METHOCEL E5LV and optionally a plasticizer. In further aspects, the water-soluble flint/fluid. may be a combination of poly¯ethylene oxide and ethanol (e.g. such as a 20% solution of polyethylene oxide and the rest a 66:33 ethanol:water mixture).

Plasticizer

The water-soluble film zone or fluid herein can also comprise one or more plasticizers. For example, it can be beneficial to add plasticizers at a level of from about 2% to about 80% or about 2% to about 60%, by weight of the soluble film zone or the water-soluble film forming polymer, or from about 10% to about 50% or from about 20° 1% to about 45° 1% by weight. The plasticizers may be, for example, glycerol, ethylene glycol, diethylene glycol, hexylene glycol, triethylene glycol, propylene glycol, polyethylene glycol, polypropyl glycol, alkyl citrate, sorbitol, pentaerythritol, glucamine, N-methylglucamine, sodiumcumenesulfonate and mixtures thereof. In one aspect, the plasticizer is glycerol. Other plasticizers may include vegetable oil, polysorbitols, polyethylene oxide, dimethicone, mineral oil, paraffin, C1-C3 alcohols, dimethyl sulfoxide, N,N-dimethylacetamide, sucrose, corn syrup, fructose, dioctyl-sodium-sulfo-succinate, triethyl citrate, tributyl citrate, 1,2-propylenglycol, mono, di- or triacetates of glycerol, natural gums, citrates, and mixtures thereof.

Optional Ingredients for Soluble Film Zone

The water-soluble film zone, fluid, or water-soluble film forming polymer herein can also comprise one or more optional ingredients. Optional ingredients include bulking agents, fillers, diluents, surfactants, stabilizing agents, emulsifiers, thickeners, preservatives, binders, colorants, pigments, solubilizing agents, wetting agents, water-soluble inert fillers, buffering agents, permeation enhancers, and combinations. Thickeners may include gum arabic, carrageenan, karaya gum, gum tragacanth, carob gum, quince seed or *Cydonia oblonga*, casein, dextrin, gelatin, sodium pectate, sodium alginate, methyl cellulose, ethyl cellulose, CMC, hydroxy ethyl cellulose, hydroxypropyl cellulose, polyvinyl alcohol, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AIMg silicate or beagum, laponite, and silicic acid anhydride.

Surfactants may include mono and diglycerides of fatty acids and polyoxyethylene sorbitol esters, such as, Atmos 300 and Polysorbate 80, pluronic acid, and sodium lauryl sulfate.

Stabilizing agents may include xanthan gum, locust bean gum and carrageenan, guar gum, sugars, polyols, amino acids or methylamines. Emulsifying agents may include triethanolamine stearate, quaternary ammonium compounds, acacia, gelatin, lecithin, bentonite, sodium benzoate.

Permeation enhancers may include azone, alcohol, dimethyl-sulfoxide, monovalent, saturated and unsaturated aliphatic and cycloaliphatic alcohols having 6 to 12 carbon atoms such as cyclohexanol, lauryl alcohol, and the like; aliphatic and cycloaliphatic hydrocarbons such as mineral oil; cycloaliphatic and aromatic aldehydes and ketones such as cyclohexanone; N,N-di(lower alkyl)acetamides such as N,N-diethyl acetamide and N,N dimethyl acetamide, N,N-dimethyl acetamide, N-(2-hy droxyethyl)acetamide and the like; aliphatic and cycloaliphatic esters such as isopropyl myristate and lauricidin; N,N-di(lower alkyl) sulfoxides such as decylmethyl sulfoxide; essential oils, nitrated aliphatics, aliphatic and cycloaliphatic hydrocarbons such as N-methyl-2-pyrrolidone and azone; salicylates, polyalkylene glycol silicates; aliphatic acids such as oleic acid and lauric acid, terpines such as cineole, siloxanes such as hexamethyl siloxane; and mixtures.

Barrier Patch

In an aspect, the barrier layer may comprise a backing layer and a pressure sensitive adhesive. In an aspect, the barrier patch may comprise a backing layer having a first surface and a second surface and a WVTR from about 1 $g/m^2/24$ b to about 500 $g/m^2/24$ b; and a pressure sensitive adhesive zone, having an upper surface and a lower surface, and the pressure sensitive adhesive may be in contact with the first surface of the backing layer.

The backing layer may be a co-extruded film laminate comprising at least two layers, but can comprise 3, 4, 5, 6, or more layers. In an aspect, the backing layer is substantially free of apertures.

"Apertures" as used herein means films having openings of a size and shape that allow for liquid molecules to pass through the film.

The barrier patch of the present invention may comprise a solid sheet material. The sheet provides the primary structure and shape to the product, allowing it to be handled and applied for treatment of a specific target area of the skin.

In certain aspects, backing layer is generally made of a flexible material which is capable of remaining fitted and flexing during the movement of the human body and movements especially associated with facial expressions or gestures. By "flexible" it is meant that the product, barrier patch, and/or the backing layer may be substantially bent or folded without breaking, tearing, ripping, etc.

In an aspect, the product or barrier patch also does not collapse or fold under gravity or upon handling and application by the user. It is desirable for the product to conform to the target area of the skin surface to which it is applied without folding, crinkling, or inducing more wrinkling of the target area of the skin. Accordingly, the product or barrier patch is readily conformable to the skin and remains flexible throughout the duration of use, as the user moves during the period worn.

In certain aspects he barrier patch, pressure sensitive adhesive, and/or the backing layer are substantially free of, comprises only non-effective amounts of, or is free of or void of, a skin active agent. As such, the barrier patch, the pressure sensitive adhesive, and/or the backing layer of the present invention may be characterized as a "blank" backing layer, adhesive, or barrier patch. In this regard, in an aspect, an effective amount of the skin active agent employed in the product herein is substantially separate from the barrier patch, the adhesive, and/or the backing layer. In an aspect, the pressure sensitive adhesive and water-soluble film are substantially separate. The term "substantially separate" as used herein means that one component is substantially free of the other component.

In one aspect, the backing layer may be a laminate comprising a film and a non-woven material for example, cotton, rayon, acrylic fibers, polypropylene fibers, polyester fibers and combinations, provided that the laminate comprises a WVTR from about 1 $g/m^2/24$ h to about 500 $g/m^2/24$ h.

The one or more layers of the backing layer or barrier patch may comprise at least one material that includes but is not limited to polypropylene (PP); polyethylene (PE), metallocene plastomers, metallocene elastomers, high density polyethylene (HDPE), rubber modified LDPE, rubber modified LLDPE, acid copolymers, polysytyrene, cyclic polyolefins, polyethylene terephthalate (PET); polyvinylchloride (PVC); polyamide (PA); polycarbonate; polyurethane; cellulose acetate; polychloropene; polysulfone; polytetrafluoroethylene (PTFE); polyvinyl acetate (PVA); polyethylene glycol terephthalate film; polystyrene; polyphenylene oxide (PPO); acrylonitrile butadiene styrene (ABS); acrylic; acrylonitrile styrene acrylate (ASA); ethylene vinyl alcohol, natural rubber, latex, nylon, nitrile, silicone and thermo plastic elastomers (TPE), ethylene vinyl acetate (EVA), ethylene acrylic acid (EAA), copolymers of PE with PP, bimodal resins, any of which may be from either homopolymers or copolymers, and blends and combinations of these materials. Blends may be physical blends or reactor blends. The layers may comprise a single polymer or mixtures of polymers or copolymers. Laminates of these layer materials may also be used.

The backing layer(s) herein may comprise polyethylene. The term "polyethylene" or "PE" is used herein the broadest sense to include PE of any of a variety of resin grades, density, branching length, copolymer, blend, catalyst, and the like. The layer may comprise a blend of different grades of polyethylene, that may include LLDPE, LDPE, VLDPE, HDPE, or MDPE, or combinations thereof; manufactured using Ziegler-Natta catalysts, chromium catalysts, metallocene based catalysts, single site catalysts, and other types of catalysts. The polymers may be homopolymers or copolymers. Blends may be physical blends or reactor blends. These materials can be bio-based, petro-based and recycled/reground. LLDPE copolymers can be made with any one or more of butene, hexene and octene comonomers. The ratio of the different grades can vary.

A preferred material for the one or more layers of the backing layer includes ethylene vinyl acetate, EVA (CAS No. 24937-78-8) copolymer. Different grades of EVAs tend to have different ethylene-to-vinyl acetate monomer ratios and/or different melt indices (molecular weights). For example, the percentage of VA monomer may range from about 20% to about 50% or from about 25% to about 40% of VA or from about 25% to about 30% of VA. For example, the melt flow index may range from about 0.7 dg/min to about 60 dg/min and/or from about 2 dg/min to about 6 dg/min and/or from about 2 dg/min to about 4 dg/min. EVA grades useful herein include Dupont Elvax® Grades: 260 (28% VA; Melt Flow Index MFI 6 dg/min via ASTM D1238); Grade 250 (28% VA; MFI 25 dg/min); Grade 150 and 150W (32% VA; MFI 43 dg/min); Grade 40 W (40% VA; MFI 52 dg/min); and Celanese Ateva® 2803G (28% VA; MFI 3 dg/min via ASTM D1238) and Ateva® 1807EG (18% VA; MFI 0.7 dg/min).

Another preferred material for the backing layer or barrier patch is a polyethylene film sold under the tradename, 1525L, available from 3M, St. Paul, Minn. 3M 1525-L has a backing of polyethylene film of approximately 3 mil thickness, a 1,4 mil thick hypoallergenic, pressure sensitive acrylate adhesive layer and a paper release layer coated with polyethylene and silicone (3M 1525L may be used without the release layer).

A color masterbatch containing pigment and/or slip/antiblock agent and/or liquid colorants can also be added to the backing layer to afford certain aesthetics and functionality. Pigments if present may typically be used in concentrations of about 0.5 wt. % to about 15 wt. %, and/or from about 1 wt. % to about 10 wt. %, or from L5 wt. % to about 7 wt. %, based on the total weight of the polymer (e.g., of the backing layer).

Other additives are further detailed in U.S. patent publications including U.S. Publication Nos. 2014/0376835, 2014/0376835, and 2014/0377512 and the references cited therein.

For example, the backing layer of the barrier patch can optionally include an additive such as a slip agent or an antistatic agent (e.g., euracarnide, a steramide), a filler (e.g., talc, clay, pulp, titanium dioxide, thermoplastic starch, raw starch wood flour, diatomaceous earth, silica, inorganic glass, inorganic salts, pulverized plasticizer, pulverized rubber), a pigment (e.g., mica, titania, carbon black), a UV inhibitor, an anti-coloring agent, a mold release agent, a flame retardant, an electrically conductive agent, an antioxidant, an impact modifier, a stabilizer (e.g., a UV absorber), wetting agents, carbon, graphene and a biodegradable-enhancing additive (e.g., an oxo-degradable additive or an organic material). An oxo-degradable additive is often compounded into a polymer in a concentration of about 1 wt. % to about 5 wt. %, based on the total weight of the polymer, and includes at least one transition metal that can foster oxidation and chain scission in plastics when exposed to heat, air, light, or mixtures thereof. Organic materials (e.g., cellulose, starch, ethylene vinyl acetate, and polyvinyl alcohol) also can be used as biodegradable-enhancing additives, although they cannot promote degradation of the non-degradable portion of the polymer matrix, In a particularly suitable example, the multi-layer co-extruded backing layer has at least three layers, including an ethylene vinyl acetate ("EVA") containing layer. In a preferred aspect, a foamed layer is in-between layers of non-foamed layers, e.g. the non-foamed first layer and the non-foamed third layer, on either side.

In one aspect, the barrier patch includes a backing layer comprising:
(i) a non-foamed first layer comprising a non-foamed polymer film having a first surface;
(ii) a foamed second layer comprising a foamed polymer film comprising a Mean Void Volume Percentage of 45% to 80%, e.g., 50% to 75% or 55% to 73%, and a thickness of 10 microns to 250 microns, e.g., 40 microns to 160 microns.

The technique for measuring Mean Void Volume Percentage is described in US Publication Nos. 2017/0112724; 2017/0112725 and 2017/0112727. The degree of foaming of a foamed layer may be characterized by a Mean Void Volume Percentage, as determined by X-ray micro-computed tomography or simply "microCT."

In one aspect, the foamed layer comprises from 45% to 80% of a Mean Void Volume

Percentage (relative to the volume of the foamed layer in total), preferably from 50% to 75%, more preferably from 55% to 73%, Mean Void Volume Percentage.

In an aspect, the backing layer of the barrier patch comprises three layers, e.g., a foamed second layer optionally comprising EVA and a layer of non-foamed EVA on either side, i.e., a first non-foamed EVA layer and a third non-foamed EVA layer wherein the foamed EVA layer is in-between said first and third non-foamed layers. The foamed layer may comprise a gas entrained therein.

In one aspect, the multi-layer barrier patch and/or the backing layer is substantially free of fiber, nanofibers, or non-woven material for example, cotton, rayon, acrylic fibers, polypropylene fibers, polyester fibers.

In another aspect, the barrier patch and/or backing layer includes a corona treatment. For example, the backing layer or barrier patch may be additionally treated, for example by corona discharge or coating with an adhesion promoter which as a primer may affect anchoring of the adhesive as well as the water-soluble film with the active.

The material composition and/or polymer resins used in the foamed layer may be different from those used in the non-foamed layer(s), since the material composition and/or resins may be optimized for foam formation, or other film layer properties. Additives, particularly small amounts of nucleating agents selected from the group consisting of $CaCO_3$, clays, talcs, and combinations thereof, may be included for quick bubble formation during foaming process.

The resin used in making the backing layer(s) of the barrier patch may include renewable materials, either "bio-identical" or "bio-new" materials, or a combination thereof. Some non-limiting options of applicable bio-identical and/or bio-new materials are further detailed in U.S. Publication Nos. 2014/0376835 2014/0377512, and 2014/0377512. For example, the barrier patch may include at least one layer made of a plastic resin. The resin could be a traditional petro-based polyolefin, or it could be a renewable based polyolefin, or a blend thereof. Alternatively, it could be a blend comprising a petro-based or renewable based polyolefin blend mixed with a renewable "bio-new" material that is chemically different to traditional petro-based polyolefins. The film layer could be comprised of a material or mixture of materials having a total bio-based content of about 10% to about 100% using ASTM D6866-10, method B. In one aspect, the layer may comprise from about 5% to about 99% by weight of a polymer (A) comprising at least one or possibly more of a low density polyethylene (LDPE), a polar copolymer of polyethylene such as ethylene vinyl acetate (EVA), a linear low density polyethylene (LLDPE), a high density polyethylene homopolymer/high density polyethylene copolymer, a medium density polyethylene, a very low density polyethylene (VLDPE), a plastomer, a polypropylene/copolypropylene/heterophasic polypropylene, polyethylene terephthalate (PET), PLA (e.g., from Natureworks), polyhydroxyalkanoate (PHA), poly(ethylene-2,5-furandicarboxylate) (PEF), cellulose (available from, for example, Innovia), nylon 11 (i.e., Rilsan® from Arkema), starch (either thermoplastic starch or starch fillers), bio-polyesters, (e.g., those made from bioglycerol, organic acid, and anhydride, as described in U.S. Publication No. 2008/0200591, incorporated herein by reference), polybutylene succinate, polyglycolic acid (PGA), and polyvinyl chloride (PVC). At least one of the constituents of polymer (A) may be at least partially derived from a renewable resource. Recycled materials may also be in added. In specific cases, materials that are biodegradable may be utilized.

Adhesive Zone

The barrier patch may comprise a backing layer and pressure sensitive adhesive. Typically, the pressure sensitive adhesive comprises a pressure-sensitive adhesive (PSA) that is suitable for long-term skin contact, and which should be physically and chemically compatible with the backing layer and/or additives that are present. Examples of suitable adhesive materials include, but are not limited to, the following: acrylic and methacrylic ester homo-or copolymers, butyl rubber based systems, silicones, urethanes, vinyl esters and amides, olefin copolymer materials, natural or synthetic rubbers, hot-melt adhesives (see, for example, U.S. Pat. No. 5,387,450); polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene) and combinations thereof.

According to one aspect the adhesive is a hotmelt adhesive including adhesives selected from the group consisting of ethyl vinyl acetate, metallocene polyalphaolefins, polyolefins including atactic polyalphaolefins, block copolymers such as diblocks copolymers and triblock copolymers, polyurethane hot melts, polyamides and combinations thereof. In one aspect, the adhesive comprises a combination of diblock copolymers and triblock copolymers. Diblocks and triblock copolymers may include styrene/isoprene; styrene/butadiene; butylene/ethylene/styrene; and combinations thereof.

High viscosity triblock copolymers may be used as adhesives and have the configuration A-B-A wherein the polymer blocks A are non-elastomeric polymer blocks which, as homopolymers have glass transition temperatures above 20° C. The elastomeric polymer blocks, B, are generally isoprene or butadiene which may be partially or substantially hydrogenated or mixtures thereof. Further, the copolymers may be linear or branched.

Diblock copolymers may generally have the A-B configuration where A and B are as described previously.

Liquid diluents may be added to the adhesive compositions. The adhesive composition may comprise from about 60% to about 99% diluents, by weight. In an aspect, the majority of the liquid diluent is oil. Preferably the liquid diluent comprises, or consists essentially of, oils such as highly refined white petroleum mineral oil. Useful diluents are primarily aliphatic in character and compatible with the polymer midblock. Plasticizers may also be included, e.g. paraffinic and naphthenic petroleum oils, highly refined aromatic-free paraffinic and naphthenic food and technical grade oils, highly refined white petroleum mineral oils, and liquid tackifiers such as the synthetic liquid oligomers of polybutene, polypropene, polyterpene, etc. The synthetic process oils may be high viscosity oligomers which may be permanently fluid /liquid monoolefins, isoparaffins or paraffins of moderate to high molecular weight.

In an aspect, the adhesive is selected from the TECHNOMELT® and DERMA-TAK® brands available from Henkel, for example TECHNOMELT PSM 154A DERMA-TAK®. DERMA-TAK products are pressure-sensitive adhesives and encompass both solvent-based acrylic and formulated rubber (liquid and hotmelt) pressure-sensitive adhesives. Useful adhesives may also be selected from those described in U.S. Patent Nos. 6,448,303 and 5,559,165.

In an aspect, the pressure sensitive adhesive is applied as continuous patterns, discontinuous patterns, or a combination thereof. The product may also comprise a plurality of discontinuous adhesive patterns.

Thickness

In one aspect, the overall total thickness of the barrier patch or the product is from 20 microns to 500 microns, preferably from 50 microns to 200 microns, more preferably from 70 to 180 microns, yet more preferably from 75 to 150 microns and combinations thereof.

In another aspect, the water-soluble film (dry state) has a total thickness of about 2 microns to about 200 microns, preferably from 50 microns to about 175 microns, more preferably from about 75 to about 170 microns. In an aspect, the water-soluble film in the dry state, has a thickness of about 5 microns to about 50 microns, or about 15 microns to about 30 microns.

In an aspect, the pressure sensitive adhesive has an average thickness ranging from about 5 microns to about 350 microns, in alternative aspects about 10 microns to about 120 microns.

In an aspect, the typical basis weight for the product herein ranges from about 40 to about 190 gsm,for instance about 45 gsm to about 170 gsm and/or from about 50 gsm to about 140 gsm.

Continuous or Discontinuous Patterns

The pressure sensitive adhesive and the water-soluble film may be comprised of continuous or discontinuous patterns. In an aspect, the adhesive and the soluble film may both be comprised of continuous patterns. In some respects, a portion of the adhesive and the soluble film are continuous and another portion may be discontinuous. By applying the soluble film and the adhesive to the backing layer in a discontinuous pattern, a portion of the skin-facing surface of the product and the adhesive remains exposed to the skin to permit sufficient adhesion, via the pressure sensitive adhesive, to the skin. In one aspect, the soluble film should be applied to the adhesive so that it covers about 1% to about 99% of the skin facing surface area of the adhesive or product, or about 10% to about 90%, and/or about 20% to about 80% of the skin facing surface area of the adhesive or the product.

The soluble film may be applied to the adhesive zone or the backing layer in a regular pattern, a random pattern, and combinations thereof. For example, the soluble film zone may be configured in either a regular or random pattern of elements such as straight lines, angled lines, curved lines, intersecting lines, dots, circles and geometric shapes, amorphous shaped, etc. or a combination of these elements.

Size and Shane of Product

The product may have a size and shape adapted to conform to a desired target area of skin which could be a human face or part thereof, legs, hands, arms, feet, or human torso. They are generally flat in appearance.

The exact size and shape of the product will depend upon the intended use and product characteristics. The product herein can be, for example, a square, circle, semicircle, rectangle, triangle, oval, ring, crescent, crescent with rounded corners, teardrop or other more complex and irregular shape. The shape of the barrier patch stay be selected from the group consisting of circle, square, rectangle, triangle, and/or irregular shape that conforms to the contours of the forehead, perioral, and/or periorbital areas of the human face.

In certain other aspects, the product comprises a size and shape to treat different areas of the face such as the forehead, the under-eye area and the under-eye area combined with the crow's feet area around the eye. Thus, the size of the product may be determined by the size of the target area of skin to be treated. Thus, a product is shaped to fit the face or the target area of skin the surface area may range from about 0.25 cm$^2$ to about 50 cm$^2$, and/or from about 1 cm$^2$ to about 30 cm$^2$, and/or from about 1 cm$^2$ to about 20 cm$^2$, and/or from about 1 cm$^2$ to about 15 cm$^2$, and/or from about 5 cm$^2$ to about 15 cm$^2$. Surface area refers to that of a flat plane having the same boundary as the surface i.e. ignoring any surface texturing present.

WVTR

According to one aspect, the backing layer or barrier patch has an WTVR value between about 1 g/m$^2$/24 h to about 500 g/m$^2$/24 h, and in another aspect, has a WVTR from about 1 g/m$^2$/24 h to about 250 g/m$^2$/24 h and/or from about 1 g/m$^2$/24 h to about 180 g/m$^2$/24 h and/or from about 2 g/m$^2$/24 h to about 150 g/m$^2$/24 h and/or from about 2 to about 20 g/m$^2$/24 h. The term WTVR stands for "Water Vapor Transmission Rate", i.e. the amount of vapor which can pass per unit area during a certain period of time.

The backing layer or barrier patch in certain aspects is non-porous or water impermeable. In certain other aspects, the multi-layer barrier patch or backing layer is impermeable to the cosmetic composition, the soluble film zone, the skin care active agent employed, and fluids wherein the WVTR is from about from about 2 to about 100 g/m$^2$/24 h. While not being bound by theory using a backing layer or barrier patch that minimizes water loss from the soluble film or cosmetic composition while in contact with the keratinous tissue and skin, prevents the water-soluble film zone or cosmetic composition, once hydrated, from drying out. This drying out may result in reduced or loss of efficacy and/or irritation to the skin.

Such relative water impermeability and lower water vapor permeability of the barrier patch may increase the effectiveness and efficiency of the cosmetic composition. For example, without being bound by theory, the relative water impermeability and lower vapor permeability of the barrier patch employed may serve to enhance or increase the penetration of the skin care active agent into the skin.

In certain aspects, the backing layer or barrier patch may, for example, consist of a perforated polyolefin film, where the size of the holes has been chosen so that air and vapor may pass, but not liquid molecules. One example of such film is described in U.S. Pat. No. 5,628 737 and/or microporous plastic films, as is described in, for example, EP-A-0238200. These laminates and films, however, are not preferred herein due to their relatively high WV IR and higher levels of breathability.

Cosmetic Composition

In an aspect, the method includes preparing a water-soluble fluid by dispersing a cosmetic composition comprising an effective amount of a skin active agent, into a water-soluble film forming polymer and mixing until homogeneous.

In an aspect, the cosmetic composition may comprise a water in oil or an oil in water emulsion to be combined with a water-soluble film forming polymer. As an example, an oil in water emulsion composition such as Olay skin care product may be combined with polyethylene oxide such as POLYOX WSR N-80 or methylcellulose or hydroxypropyl methylcellulose such as METHOCEL E5LV and used as the water-soluble film zone. The water-soluble film forming polymer may be used in excess of the composition comprising the oil in water emulsion and skin active agent. In an aspect, thus, the water-soluble film zone may comprise:

a.) from about 40% to about 70%, preferably from 52% to 70%, by weight of the soluble film zone, of a water-soluble film forming polymer;

b.) from about 30% to about 60% by weight of the soluble film zone, of a cosmetic composition comprising a water in oil or an oil in water emulsion and an effective amount of a skin active agent and optionally a safe and effective amount of a plasticizer.

In an aspect, the ratio of b) to a) in the soluble film zone, is from about 30:70 to about70:30 or from about 40:60 to about 60:40 or about 45:55 to about 55:45 in either the wet or dry state.

Skin Active Agents

In one aspect, the product provides an effective amount of a skin active agent to be delivered to the target area of skin. In another aspect, the product provides from about 0.5 mg/cm$^2$ to about 3 mg/cm$^2$ of the cosmetic composition, and/or from about 1 mg/cm$^2$ to about 2 mg/cm$^2$ to the target area of skin. In one aspect and without being bound by theory, the use of the proper amount of the cosmetic composition will minimize the interaction of the cosmetic composition with the pressure sensitive adhesive. The compositions of the present invention may comprise a skin active agent which provides a skin care benefit characteristic of the usage of the skin care product. The skin care benefit may include benefits related to appearance or make-up of the skin. The skin care active can provide acute (immediate and short lived) benefits, or chronic (long term and longer lasting) benefits.

The term "skin active agent" as used herein, means an active ingredient which provides a cosmetic and/or therapeutic effect to the area of application on the skin. The skin active agents useful herein include skin lightening agents, anti-acne agents, emollients, non-steroidal anti-inflammatory agents, topical anesthetics, artificial tanning agents, anti-microbial and anti-fungal actives, skin soothing agents, sun screening agents, skin barrier repair agents, anti-wrinkle agents, anti-skin atrophy actives, lipids, sebum inhibitors, sebum inhibitors, skin sensates, protease inhibitors, anti-itch agents, desquamation enzyme enhancers, anti-glycation agents, diaper rash agents, anti-eczema agents, botanicals, vitamin B3 compounds, N-acyl amino acid compounds, and mixtures thereof. When included, the present composition comprises a safe and effective amount of a skin active agent and/or from about 0.0001% to about 20%, in another aspect from about 0.01% to about 10% of at least one skin active agent.

The cosmetic compositions may include from about 0.00001 to about 10% by weight of botanical actives or from about 0.01 to about 8 percent by weight, or from about 0.05 to about 5 percent by weight. "Botanical" herein means a substance, extract or derivative of a plant and may also be described as "herbals". Botanicals may include water-soluble or oil-soluble active materials extracted from a particular plant including materials extracted from echinacea, yucca glauca, willow herb, basil leaves, Turkish oregano, carrot root, grapefruit fruit, fennel fruit, rosemary, thyme, blueberry, bell pepper, black tea, blackberry, black currant fruit, Chinese tea, coffee seed, dandelion root, date palm fruit, gingko leaf, green tea polyphenols (e.g. epicatechin gallate and epigallocatechin 3-O-gallate), hawthorn berries, licorice, oolong tea, sage, strawberry, sweet pea, tomato, vanilla fruit, neohesperidin, quercetin, rutin, morin, rnyricetin, chlorogenic acid, glutathione, glycyrrhizin, absinthe, arnica, centella asiatica, chamomelle, comfrey, cornflower, horse chestnut, ivy (Herdera helix), magnolia, mimosa, oat extract, pansey, scullcap, seabuckthom, white nettle, witch hazel and any combinations thereof.

The type and amount of skin active agents are selected so that the inclusion of a specific agent does not affect the stability of the composition. For example, hydrophilic agents may be incorporated in an amount soluble in the aqueous phase, while lipophilic agents may be incorporated in an amount soluble in the oil phase.

Skin active agents are also disclosed in US Publication No. 2007/0020220A1, published Jan. 25, 2007, wherein the components/ingredients are incorporated herein by reference in their entirety.

The cosmetic composition may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide also refers to both naturally occurring and synthesized peptides. In one aspect, the peptides are di-, tri-, tetra-, penta-, and hexa-peptides, their salts, isomers, derivatives, and mixtures thereof. Examples of useful peptide derivatives include, but are not limited to, peptides derived from soy proteins, palmitoyl-lysine-threonine (pal-KT) and pahnitoyl-lysine-threonine-threonine-lysine-serine (pal-KTTKS, available in a composition known as MATRIXYL®) palmitoyl-glycine-glutamine-proline-arginine (pal-GQPR, available in a composition known as RIGIN®), these three being available from Sederma, France, and Cu-histidine-glycine-glycine (Cu-HGG, also known as IAMIN®). In various aspects, the cosmetic composition may comprise from about $1 \times 10^{-7}\%$ to about 20%, alternatively from about $1 \times 10^{-6}\%$ to about 10%, and alternatively from about $1 \times 10^{-5}\%$ to about 5% of the peptide.

In one aspect, the skin active agent is niacinamide. In one aspect, the agent is a combination of niacinamide, glycerin, tocopherol acetate, and D-panthenol. Niacinamide may be included in the composition in an amount between about 1% to about 30 wt %, in another aspect from about 2% to about 28 wt %, in another aspect from about 5% to about 25 wt %, and in another aspect from about 10% to about 20 wt %. When D-panthenol is included, it may be present in an amount of about 0.5% to about 5 wt %, or about 0.5% to about 3 wt % and/or about 0.5% to about 2 wt %. Glycerin may be included as an active in an amount from about 6% to about 20 wt %, and/or from about 8% to about 15 wt %, and/or from about 10% to about 15 wt %.

In various aspects, the skin active agent is selected from niacinamide, alone or in combination with one or more of palmitoyl-lysine-threonine, palmitoyl-lysine-threonine-threonine-lysine-serine, N-undecyl-10-enoyl-L-phenylalanine, retinyl propionate, N-acetyl glucosamine, vitamin C, tretinoin, salicylic acid, benzoic acid, benzoyl peroxide, tretinoin, and combinations thereof.

In an aspect, the cosmetic compositions herein may be aqueous solutions, or emulsions such as oil-in-water emulsions, water-in-oil emulsions or multiple emulsions having aqueous or oily external phases. In another aspect, the cosmetic compositions herein are oil-in-water emulsions.

In one aspect to avoid a negative interaction with the pressure sensitive adhesive, the cosmetic composition or water-soluble film zone comprises only low levels of silicones of about 0.5% to about 10%, and/or from about 1% to about 5% and/or the cosmetic composition is substantially free of silicones. As used herein "silicones" may refer to those silicones disclosed in US 2007/0020220.

In one aspect, the cosmetic composition is substantially free of depilatory agents.

The cosmetic composition may comprise an effective amount of a skin active agent having activity to improve visual or aesthetic appearance of the skin, such as an agent effective to reduce or diminish the appearance of fine lines and/or wrinkles on human facial skin or an agent effective to treating existing acne lesions, reducing redness associated with acne lesions and/or protecting from formation of acne lesions.

In another aspect, a method of treating skin is provided, comprising applying the product to a target area of the skin, comprising an effective amount of a skin active agent.

The methods of treatment, application, regulation, or improvement disclosed herein may utilize the product and/or multi-layer barrier patch. Application of the present product can occur on any target area of skin surface of the body. Skin surfaces of the most concern tend to be those not typically covered by clothing such as facial skin surfaces, hand and arm skin surfaces, foot and leg skin surfaces, and neck and chest skin surfaces (e.g., décolletage). Application may be on a facial skin surface including the forehead, perioral, chin, periorbital, nose, and/or cheek skin surfaces.

The step of applying the product to a target area of skin may be done by localized application to the target area, for example an area that contains wrinkles. In reference to the application, the term "localized", "local", or "locally" mean that it is delivered to the target area of skin (such as an area of skin containing wrinkles) while minimizing delivery to skin surface not requiring treatment.

One or more products of the present invention can be applied broadly to one or more facial skin surfaces to reduce the appearance of wrinkles within those facial skin regions.

The method of treating skin herein may optionally begin with a cleansing step. The consumer can wash his or her face with a suitable cleanser (e.g., Olay Purifying Mud Lathering Cleanser, available from The Procter & Gamble Company, Cincinnati, Ohio), and gently dry his or her skin.

The product may be applied to at least one target portion of skin selected from the group consisting of a forehead, perioral, chin, periorbital, nose, cheek, skin surface, and combinations thereof. The product may be applied to the target portion of skin for a treatment period. The treatment period may comprise at least once a day for at least four weeks, preferably applied at least twice a day for at least four weeks, more preferably at least once a day for at least eight weeks, and more preferably at least twice a day for at least eight weeks, preferably the length of the treatment period is at least 2 weeks, preferably at least 4 weeks, and more preferably at least 8 weeks. The product may remain on the target portion of skin for about 1 minute to about 24 hours or from about 2 hours to about 10 hours, prior to the removal from the skin. In an aspect, the target portion of skin comprises a hyperpigmented spot, wrinkles, fine lines, dryness, skin laxity and combinations thereof.

Test Methods

WVTR

WVTR of the barrier patch (the backing layer combined with the pressure sensitive adhesive layer) or backing layer is measured according to ASTM F1249 13 at 37° C. and 35% RH. Samples may be analyzed on a MOCON Permatran-W 3/33 Water Vapor Permeability Instrument using ASTM F1249. For samples with higher WVTR (e.g. from approximately 300 g/m$^2$/24 h to 500 g/m$^2$/24 h) samples may be analyzed per ASTM E-96 with desiccant placed inside the test cups and 35% RH surrounding the exterior of the cups. Samples of barrier patches are prepared and do not include the pressure sensitive adhesive.

Basis Weight

Basis Weight is calculated as follows. Sample Preparation: Samples were equilibrated at TAPPI conditions for 100 hours (50% RH, 23° C.). Cut samples to 25.4 mm wide strips using JDC 1" strip cutter. Cut samples to 80 mm long using gage block. Weigh each sample using 4 place analytical balance. Basis weight is calculated as the sample mass/area, where mass is measured on the balance and area=25.4 mm×80 mm=2032 mm=0.002032 meters. Basis weight is reported in units of grams/meter$^2$.

Caliper/Thickness

Thickness measurement may be performed using ASTM D5729 which typically uses a pad caliper with a known pressure (0.1 psi) and a gage sensor. A Qualitest Thickness Tester, Model CHY-C2, available from www.WorldofTest.com may be used.

Dissolution Method

The water-soluble film is aged for 24 hours at 21° C. (+/−1.5° C.) and 50% relative humidity (+1-1.5% relative humidity). Cut three test specimens of the water-soluble film sample to a size of 3.8 cm×3.2 cm. Lock each specimen in a separate 35 mm slide mount. Fill a suitable beaker with 500 mL of distilled water, and maintain a constant temperature of 20° C. Mark height of column of water. Place beaker on magnetic stirrer, add magnetic stirring rod to beaker, turn on stirrer, and adjust stir speed until a vortex develops which is approximately one-fifth the height of the water column. Mark depth of vortex. Secure the 35-mm slide mount in an alligator clamp of a slide mount holder, such that the long end of the slide mount is parallel to the water surface. The depth adjuster of the holder should be set so that when dropped, the end of the clamp will be 0.6 cm below the surface of the water. One of the short sides of the slide mount should be next to the side of the beaker with the other positioned directly over the center of the stirring rod such that the film surface is perpendicular to the flow of the water. In one motion, drop the secured slide and clamp into the water and start the timer. When all visible film is released from the slide mount, raise the slide out of the water while continuing to monitor the solution for undissolved film fragments. For each sample, record the time when all film fragments of each sample are no longer visible to the naked eye, and the solution becomes clear. Average the time values for the 3 samples and if the average time is 15 minutes or less, then the sample constitutes a water-soluble film.

Adhesive Release Force

Adhesion measurements from polyethylene terepthalate transfer substrate films were evaluated with a ChemInstruments AR1000. Specimens are cut to segments 1.9 cm wide. Specimens are placed onto a stainless-steel test panel that has been covered with polyethylene terephthalate (Octi Films). Specimens are then rolled with a 2.04 kg hand-roller. The panel is placed into the instrument at room temperature and one end of the specimen is attached to the grip set at a 180° peel using Nexcare® gentle paper tape (1.9 cm wide) as a coupler. The speed is set to 25.4 cm/minute and the measurement is initiated. After data collection, the initial (onset of pull) and final (pull-off) regions are discarded and the central region where there is constant pull against the specimen are used to generate an average peel force. Peel forces from three specimens are averaged to generate a peel force for each sample.

Viscosity of Water Suitable Fluid

The viscosity values of the water-soluble fluid can be measured on a suitable rheometer, such as a TA Instruments AR1500EX Rheometer, with 40 mm diameter parallel plates and a 1000-micron gap at a shear rate of 0.1 reciprocal seconds for a period of 5 seconds at 25° C. (available from TA Instruments, New Castle, Del.).

EXAMPLES

The following are non-limiting examples of products and methods of the present invention. The examples are given solely for illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the ingredients selected to make the present invention as described herein.

A. Preparation of Beauty Care Product:

The following formulation and procedure is used to make an emulsion from the individual ingredients.

|  | Component | Weight % |
|---|---|---|
| Solution A | PEG 100 Stearate (surfactant) | 1% |
|  | Emulgade PL 68-50[1] (surfactant) | 1% |
|  | Eutanol G 16[2] (hexyldecanol) | 10% |
| Solution B | Sepiwhite MSH (Undecylenoyl phenylalanine)[3] | 0.4% |
|  | 1N Sodium Hydroxide solution | 1.26% |
| Solution C | Water | 52.34% |
|  | Niaciniamide | 10% |
|  | Glycerol | 20% |
|  | Inositol | 4% |

[1]Available from BASF.
[2]Available from BASF.
[3]Available from BASF.

Mix the ingredients of Solution A and heat to 80° C. with stirring. Then place Solution B ingredients into a small beaker and stir until the solution becomes clear to deprotonate the Sepiwhite MSH to make it soluble in water. Then heat ingredients of Solution C to 80° C. with stirring.

Add Solution B slowly to Solution C with rapid stirring for 10 minutes. Then add Solution A slowly over 15 minutes with rapid stirring at 80° C. and stir for 30 minutes and then mill with a hand-held mill for 2 minutes at 80° C. Stir the solution and allow to cool to RT. Once at RT, place the solution into a jar and label. After 96 hours, the solution is stable with no separation and no solids forming.

Once the above emulsions are obtained, to make the water-soluble fluid, mix a 60:40 ratio mixture of polymer solution to emulsion. Prepare the polymer solution as follows. Place 799.8 g of distilled water into a beaker and stir with an overhead mixer at 500 RPMs. Next, add 0.2 g of phenoxyethanol and stir. Once dispersed, slowly add 200 g of 200 k PEO, Polyox WSR N-80, with a molecular weight of about 200,000 available from Dow, over 45 minutes. Continue stirring at 500 RPMs for 30 minutes. Next, slow the stirring to 200 RPMs and stir for 2 hours. Then mix the polymer solution with the emulsion at a 60:40 ratio mixture of polymer solution to emulsion. Mix until homogeneous to achieve a viscosity of about 30,000 cP to about 50,000 cP.

Alternatively, an emulsion (oil in water or water in oil) that is a commercially available beauty composition (e.g. an Olay skin care emulsion product), comprising an effective amount of a skin active agent, may be used instead of preparing an emulsion from the individual ingredients.

Polymer Solution with PEO in Ethanol/Water

An alternative polymer solution may be used and is prepared as follows. Place 535.8 g of ethanol in a beaker and stir with an overhead mixer at 300 RPMs. Then add 0.2 g of phenoxyethanol stir. Once dispersed, add 200 g of 200 k PEO (Polyox WSR N-80, with a molecular weight of about 200,000 available from Dow) and stir at 300 RPMs for 15 minutes to disperse. Once dispersed, add 264 g of distilled water and stir at 100 RPMs for 2 hours. Then mix the polymer solution with the emulsion at a 60:40 ratio mixture of polymer solution to emulsion. Mix until homogeneous to achieve a viscosity of about 30,000 cP to about 55,000 cP.

Methocel Polymer Solution

An alternative polymer solution may be used and is prepared as follows. Place 799.8 g of distilled water in a beaker and heat to 95° C. with stirring from an overhead mixer at 300 RPMs. Once at 95° C., add 0.2 g of phenoxyethanol and stir until dispersed. Next, add Methocel E5LV powder with stirring at 300 RPMs. Once all the Methocel E5LV is added, remove heat and stir the mixture at 300 RPMs until at 60C. Once at 60° C., turn down the stirring to 150 RPMs and place the beaker in an ice bath and stir until completely hydrated, usually overnight. Then mix the polymer solution with the emulsion at a 60:40 ratio mixture of polymer solution to emulsion. Mix until homogeneous to achieve a viscosity of about 30,000 cP to about 55,000 cP.

The polymer solutions may be prepared with solvents selected from the group consisting of water, ethanol, isopropanol, propanol, and other water-soluble solvents such as alcohols, glycols, and combinations thereof.

Backing and Adhesive Layer

A backing layer according to Sample 3 of Provisional U.S. Patent Application Ser. No. 62/257,341, filed on Nov. 19, 2015, is provided. Sample 3 is a 3-layer film having a foamed core layer and non-foamed outer layers. All layers are made of EVA. The outside layers each have approximately 20 μm thickness and the core foamed layer has approximately 130 μm thickness. The total thickness of the backing layer is approximately 170 μm. The basis weight is about 99 gsm and the WVTR is 82 g/m²/24 hours. The backing layer has a first surface.

Alternatively, the backing layer may comprise a low-density polyethylene film or a non-foamed laminate of EVA. The backing layer or barrier patch may also comprise a polyethylene film sold under the tradename. 3M 1525L, available from 3M, St. Paul, Minn, (without the release layer) which has a backing of polyethylene film of approximately 76.2 microns thickness and a 35.6 microns thick hypoallergenic, pressure sensitive acrylate adhesive layer.

Slot coat a pressure sensitive adhesive (if an adhesive is not already present with the backing layer), such as for example, TECHNOMELT® and DERMA-TAK® brands available from Henkel, (for example TECHNOMELT PSM 154A DERMA-TAK®) at a basis weight of about 50 g/m² to about 160 g/m² or specifically about 95 g/m², on the first surface of the backing layer. The pressure sensitive adhesive comprises a continuous layer across the first surface of the backing layer.

Transfer Substrate and Image Carrier Screen

Prepare a transfer substrate having a first surface, wherein the transfer substrate is PET (Polyethylene Terephthalate). Prepare an image carrier screen having an upper side and a lower side and a plurality of channels and having a mesh or pore size corresponding to about 200 to about 250 mesh. Then position the transfer substrate under the lower side of the image carrier screen with the first surface of the transfer substrate in contact the lower side of the image carrier screen. Apply the above prepared water-soluble fluid to the upper side of the image carrier screen whereby the transfer substrate is coated with the fluid through the channels of the image carrier screen. Dry the fluid to a film having total thickness of about 5 microns to form a water-soluble film. The coat weight of the fluid is about 1 mg/in² to about 4 mg/in². Then remove the image carrier screen. A Gardo Draw Down table and a #44 Draw Down bar, may be used.

Then apply force to separate the dry water-soluble film from the transfer substrate by contacting the pressure sensitive adhesive side of the backing layer to the dry water-soluble film. The soluble film is thus coated as a discontinuous or continuous layer on the upper (outer) surface of the pressure sensitive adhesive layer/zone. The soluble film has a coating basis weight from about 30 g/m² to about 200 g/m². A multi-layer beauty care product is thus formed.

The Product of the above examples may be attached via the adhesive side to the periorbital area for treatment of periorbital skin aging. The Product is applied and worn for an extended period of approximately 7-8 hours such as overnight, and thereafter removed. The Products herein deliver an effective amount of the skin active agent in a manner that achieves penetration of the skin active agent into the stratum corneum, and/or other layers of the epidermis, and in some aspects, into the basal skin layer and/or Bennis.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of producing a multi-layer beauty care product for applying a skin active agent to skin, comprising:
    providing a transfer substrate having a first surface;
    preparing a water-soluble fluid by
        dispersing a cosmetic composition comprising an effective amount of a skin active agent into a water-soluble film forming polymer and mixing until homogeneous to achieve a viscosity of about 25,000 cP to about 85,000 cP, and
        providing an image carrier screen having an upper side and a lower side and a plurality of channels and having a mesh size of about 40 mesh to about 500 mesh;
    positioning the transfer substrate under the lower side of the image carrier screen with the first surface of the transfer substrate in contact the lower side of the image carrier screen;
    applying the water-soluble fluid to the upper side of the image carrier screen, whereby the transfer substrate is coated with the fluid through the channels of the image carrier screen;
    removing the image carrier screen;
    drying the water-soluble fluid to form a water-soluble film;
    providing a backing layer having a first surface and a second surface and a water vapor transmission rate (WVTR) of about 1 g/m²/24 h to about 500 g/m²/24 h;
    applying a pressure sensitive adhesive to the first surface of the backing layer, whereby at least a portion of the backing layer is coated with the pressure sensitive adhesive to form a pressure sensitive adhesive side of the backing layer; and
    separating the dry water-soluble film from the transfer substrate by contacting the pressure sensitive adhesive side of the backing layer to the dry water-soluble film and by applying a force to separate the dry water-soluble film from the transfer substrate to form the multi-layer beauty care product.

2. The method of claim 1, wherein the force to separate the dry water-soluble film from the transfer substrate is less than the force to separate the film from the pressure sensitive adhesive.

3. The method of claim 1, wherein the force to separate the dry water-soluble film from the transfer substrate is about 175 g/2.54 cm to about 700 g/2.54 cm.

4. The method of claim 1, wherein the pressure sensitive adhesive is applied to about 50% to 100% of the total surface area of the first surface of the backing layer.

5. The method of claim 1, wherein the pressure sensitive adhesive is applied as a continuous film or a discontinuous film onto the backing layer.

6. The method of claim 1, wherein the pressure sensitive adhesive is applied around an outer perimeter of the first surface of the backing layer.

7. The method of claim 1, wherein the pressure sensitive adhesive is selected from the group consisting of acrylic and methacrylic ester homo-or copolymers, butyl rubber-based systems, silicones, urethanes, vinyl esters and amides, olefin copolymer materials, and combinations thereof.

8. The method of claim 1, wherein the pressure sensitive adhesive is free of a skin active agent.

9. The method of claim 1, wherein the image carrier screen comprises a patterned film on the lower side of the image carrier screen and wherein the first surface of the transfer substrate is in contact with the pattern film surface of the image carrier screen.

10. The method of claim 1, wherein the water-soluble fluid is applied to the transfer substrate as discontinuous zones corresponding to the plurality of openings of the pattern film or the plurality of channels of the image carrier screen.

11. The method of claim 10, wherein the water-soluble fluid is applied to the transfer substrate as a continuous border around the perimeter corresponding to the plurality of openings of the pattern film.

12. The method of claim 1 wherein the fluid comprises about 10% to about 60% of a water-soluble film forming polymer.

13. The method of claim 1, wherein the dry water-soluble film has a total thickness of about 2 microns to about 75 microns.

14. The method of claim 1, wherein the water-soluble fluid has a coating weight from about 1 mg/in² to about 4 mg/in².

15. The method of claim 1, wherein the transfer substrate is selected from the group consisting of polyethylene terephthalate, biaxially-oriented polyethylene terephthalate, and combinations thereof.

16. The method of claim 1, further comprising drying the water-soluble fluid at a drying temperature of about 20° C. to about 250° C.

17. The method of claim 1, wherein the water-soluble fluid comprises polyethylene oxide and methylcellulose or hydroxypropyl methylcellulose.

18. The method of claim 16, wherein the water-soluble fluid comprises polyethylene oxide polymer and ethanol, and optionally a plasticizer.

19. A method of producing a multi-layer beauty care product for applying a skin active agent to the skin, comprising:
    providing a transfer substrate having a first surface;
    preparing a water-soluble fluid by:
        dispersing a cosmetic composition comprising an effective amount of a skin active agent into a water-soluble film forming polymer and mixing until homogeneous,
        wherein the film forming polymer comprises a water-soluble polymer selected from the group consisting of polyethylene oxide, methylcellulose, hydroxypropyl methylcellulose, and combinations thereof;
    providing an image carrier screen having an upper side and a lower side;
    positioning the transfer substrate under the lower side of the image carrier screen with the first surface of the transfer substrate in contact the lower side of the image carrier screen;
    applying the water-soluble fluid to the upper side of the image carrier screen, whereby the transfer substrate is coated with the fluid through the channels of the image carrier screen;
    removing the image carrier screen;
    drying the fluid to a film having a total thickness;
    providing a backing layer having a first surface and a second surface;
    applying a pressure sensitive adhesive to the first surface of the backing layer, whereby the backing layer is coated with the pressure sensitive adhesive to form a pressure sensitive adhesive side of the backing layer; and separating the dry water-soluble film from the transfer substrate by contacting the pressure sensitive adhesive side of the backing layer to the dry water-soluble film and applying a force to separate the dry water-soluble film from the transfer substrate to form the multi-layer beauty care product.

* * * * *